(12) United States Patent
Jeppesen et al.

(10) Patent No.: US 6,353,018 B1
(45) Date of Patent: Mar. 5, 2002

(54) COMPOUNDS, THEIR PREPARATION AND USE

(75) Inventors: Lone Jeppesen, Virum; Paul Stanley Bury, København; Per Sauerberg, Farum, all of (DK)

(73) Assignees: Novo Nordisk A/S, Bagsvaerd (DK); Dr. Reddy's Research Foundation, Hyderabad (IN)

( * ) Notice: Subject to any disclaimer, the term of this patent is extended or adjusted under 35 U.S.C. 154(b) by 0 days.

(21) Appl. No.: 09/421,172

(22) Filed: Oct. 19, 1999

(30) Foreign Application Priority Data

Oct. 21, 1998 (DK) ......................... 1998 01353

(51) Int. Cl.[7] ................. A61K 31/38; A61K 31/35; C07D 333/76; C07D 311/80
(52) U.S. Cl. ................. 514/437; 514/454; 549/46; 549/390
(58) Field of Search ................. 549/46, 390; 514/437, 514/454

(56) References Cited

U.S. PATENT DOCUMENTS 6,048,856 A * 4/2000 Jorgensen et al. .......... 514/217

FOREIGN PATENT DOCUMENTS

| WO | WO 96/04260 | 2/1996 |
| WO | WO 96/04261 | 2/1996 |
| WO | WO 97/25042 | 7/1997 |
| WO | WO 97/36579 | 10/1997 |
| WO | WO 99/19313 | 4/1999 |

OTHER PUBLICATIONS

Abstract of Japanese Patent No. JP 10182550, Jul. 1998.

* cited by examiner

Primary Examiner—Bruce Kifle
(74) Attorney, Agent, or Firm—Reza Green, Esq.; Peter J. Waibel, Esq.

(57) ABSTRACT

The present invention relates to compounds of the general formula (I)

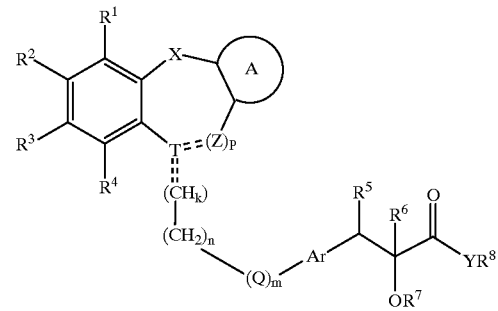

(Ia)

The compounds are useful in the treatment and/or prevention of conditions mediated by nuclear receptors, in particular the Peroxisome Proliferator-Activated Receptors (PPAR).

14 Claims, No Drawings

COMPOUNDS, THEIR PREPARATION AND USE

CROSS-REFERENCE TO RELATED APPLICATIONS

This application claims priority under 35 U.S.C. 119 of Danish application PA 1998 01353 filed Oct. 21, 1998, and of U.S. Provisional application 60/106,000 filed Oct. 28, 1998, the contents of which are fully incorporated herein by reference.

FIELD OF INVENTION

The present invention relates to novel compounds, pharmaceutical compositions containing them, methods for preparing the compounds and their use as medicaments. More specifically, compounds of the invention can be utilised in the treatment of conditions mediated by nuclear receptors, in particular the Peroxisome Proliferator-Activated Receptors (PPAR).

The present compounds reduce blood glucose and triglyceride levels and are accordingly useful for the treatment of ailments and disorders such as diabetes and obesity.

The present invention also relates to a process for the preparation of the above said novel compounds, their derivatives, their analogs, their tautomeric forms, their stereoisomers, their polymorphs, their pharmaceutically acceptable salts, pharmaceutically acceptable solvates and pharmaceutical compositions containing them.

The compounds are useful for the treatment and/or prophylaxis of insulin resistance (type 2 diabetes), impaired glucose tolerance, dyslipidemia, disorders related to Syndrome X such as hypertension, obesity, insulin resistance, hyperglycaemia, atherosclerosis, hyperlipidemia, coronary artery disease and other cardiovascular disorders. The compounds of the present invention are also useful for the treatment of certain renal diseases including glomerulonephritis, glomerulosclerosis, nephrotic syndrome, hypertensive nephrosclerosis. These compounds may also be useful for improving cognitive functions in dementia, treating diabetic complications, psoriasis, polycystic ovarian syndrome (PCOS) and prevention and treatment of bone loss, e.g. osteoporosis.

BACKGROUND OF THE INVENTION

Coronary artery disease (CAD) is the major cause of death in type 2 diabetic and metabolic syndrome patients (i.e. patients that fall within the 'deadly quartet' category of impaired glucose tolerance, insulin resistance, hypertriglyceridaemia and/or obesity).

The hypolipidaemic fibrates and antidiabetic thiazolidinediones separately display moderately effective triglyceride-lowering activities although they are neither potent nor efficacious enough to be a single therapy of choice for the dyslipidaemia often observed in type 2 diabetic or metabolic syndrome patients. The thiazolidinediones also potently lower circulating glucose levels of type 2 diabetic animal models and humans. However, the fibrate class of compounds are without beneficial effects on glycaemia. Studies on the molecular actions of these compounds indicate that thiazolidinediones and fibrates exert their action by activating distinct transcription factors of the peroxisome proliferator activated receptor (PPAR) family, resulting in increased and decreased expression of specific enzymes and apolipoproteins respectively, both key-players in regulation of plasma triglyceride content. Fibrates, on the one hand, are PPAR$\alpha$ activators, acting primarily in the liver. Thiazolidinediones, on the other hand, are high affinity ligands for PPAR$\gamma$ acting primarily on adipose tissue.

Adipose tissue plays a central role in lipid homeostasis and the maintenance of energy balance in vertebrates. Adipocytes store energy in the form of triglycerides during periods of nutritional affluence and release it in the form of free fatty acids at times of nutritional deprivation. The development of white adipose tissue is the result of a continuous differentiation process throughout life. Much evidence points to the central role of PPAR$\gamma$ activation in initiating and regulating this cell differentiation. Several highly specialised proteins are induced during adipocyte differentiation, most of them being involved in lipid storage and metabolism. The exact link from activation of PPAR$\gamma$ to changes in glucose metabolism, most notably a decrease in insulin resistance in muscle, has not yet been clarified. A possible link is via free fatty acids such that activation of PPAR$\gamma$ induces Lipoprotein Lipase (LPL), Fatty Acid Transport Protein (FATP) and Acyl-CoA Synthetase (ACS) in adipose tissue but not in muscle tissue. This, in turn, reduces the concentration of free fatty acids in plasma dramatically, and due to substrate competition at the cellular level, skeletal muscle and other tissues with high metabolic rates eventually switch from fatty acid oxidation to glucose oxidation with decreased insulin resistance as a consequence.

PPAR$\alpha$ is involved in stimulating $\beta$-oxidation of fatty acids. In rodents, a PPAR$\alpha$-mediated change in the expression of genes involved in fatty acid metabolism lies at the basis of the phenomenon of peroxisome proliferation, a pleiotropic cellular response, mainly limited to liver and kidney and which can lead to hepatocarcinogenesis in rodents. The phenomenon of peroxisome proliferation is not seen in man. In addition to its role in peroxisome proliferation in rodents, PPAR$\alpha$ is also involved in the control of HDL cholesterol levels in rodents and humans. This effect is, at least partially, based on a PPAR$\alpha$-mediated transcriptional regulation of the major HDL apolipoproteins, apo A-I and apo A-II. The hypotriglyceridemic action of fibrates and fatty acids also involves PPAR$\alpha$ and can be summarised as follows: (I) an increased lipolysis and clearance of remnant particles, due to changes in lipoprotein lipase and apo C-II levels, (II) a stimulation of cellular fatty acid uptake and their subsequent conversion to acyl-CoA derivatives by the induction of fatty acid binding protein and acyl-CoA synthase, (III) an induction of fatty acid b-oxidation pathways, (IV) a reduction in fatty acid and triglyceride synthesis, and finally (V) a decrease in VLDL production. Hence, both enhanced catabolism of triglyceride-rich particles as well as reduced secretion of VLDL particles constitutes mechanisms that contribute to the hypolipidemic effect of fibrates.

A number of compounds have been reported to be useful in the treatment of hyperglycemia, hyperlipidemia and hypercholesterolemia (U.S. Pat. No. 5,306,726, PCT Publications nos. WO91/19702, WO 95/03038, WO 96/04260, WO 94/13650, WO 94/01420, WO 97/36579, WO 97/25042, WO 95/17394, WO 99/08501, WO 99/19313 and WO 99/16758).

SUMMARY OF THE INVENTION

It seems more and more apparent that glucose lowering as a single approach does not overcome the macrovascular complications associated with type 2 diabetes and metabolic syndrome. Novel treatments of type 2 diabetes and metabolic syndrome must therefore aim at lowering both the overt hypertriglyceridaemia associated with these syndromes as well as alleviation of hyperglycaemia.

The clinical activity of fibrates and thiazolidinediones indicates that research for compounds displaying combined PPAR α and PPAR γ activation should lead to the discovery of efficacious glucose and triglyceride lowering drugs that have great potential in the treatment of type 2 diabetes and the metabolic syndrome (i.e. impaired glucose tolerance, insulin resistance, hypertriglyceridaemia and/or obesity).

DETAILED DESCRIPTION OF THE INVENTION

Accordingly, the present invention relates to compounds of the general formula (Ia):

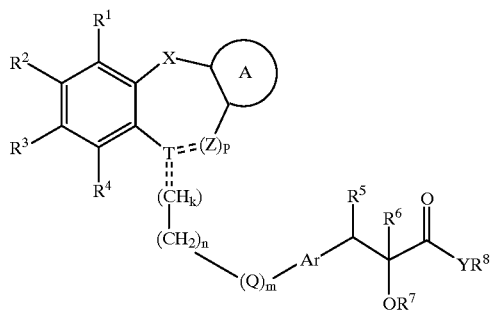

(Ia)

wherein $R^1$, $R^2$, $R^3$, and $R^4$ independently of each other represent hydrogen, halogen, perhalomethyl, hydroxy, nitro, cyano, formyl, or $C_{1-12}$alkyl, $C_{4-2}$-alkenynyl, $C_{2-12}$-alkenyl, $C_{2-12}$-alkynyl, $C_{1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-12}$alkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR$^{11}$, or —SO$_2$R$^{12}$, wherein $R^{11}$ and $R^{12}$ independently of each other are selected from hydroxy, halogen, perhalomethyl, $C_{1-6}$alkoxy or amino optionally substituted with one or more $C_{1-6}$alkyl, perhalomethyl or aryl; optionally substituted with one or more halogen, perhalomethyl, hydroxy, nitro or cyano; or $R^1$ and $R^2$, $R^2$ and $R^3$ and/or $R^3$ and $R^4$ may form a cyclic ring containing from 5 to 7 carbon atoms optionally substituted with one or more $C_{1-6}$alkyl; ring A represents a 5–6 membered cyclic ring, optionally substituted with one or more halogen, perhalomethyl, hydroxy, nitro, cyano, formyl, or $C_{1-12}$alkyl, $C_{4-12}$-alkenynyl, $C_{2-12}$-alkenyl, $C_{2-12}$-alkynyl, $C_{1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-12}$alkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR—, or —SO$_2$R$^{12}$, wherein $R^{11}$ and $R^{12}$ independently of each other are selected from hydroxy, halogen, perhalomethyl, $C_{1-6}$alkoxy or amino optionally substituted with one or more $C_{1-6}$alkyl, perhalomethyl or aryl; optionally substituted with one or more halogen, perhalomethyl, hydroxy, nitro or cyano;

X is a valence bond, —(CHR$^9$)—, —(CHR$^9$)—CH$_2$—, —CH═CH—, —O—, —O—(CHR$^9$)—, —S—(CHR$^9$)—, —(NR$^9$)—CH$_2$—, —(CHR$^9$)—CH═CH—, —(CHR$^9$)—CH$_2$—CH$_2$—, —(C═O)—, —O—CH$_2$—O—, —(NR$^9$)—, —(NR$^9$)—S(O$_2$)—, —CH═(CR$^9$)—, —(CO)—(CHR$^9$)—, —CH$_2$—(SO)—, —S—, —(SO)—, —(SO$_2$)—, —CH$_2$—(SO$_2$)—, —CH$_2$—O—CH$_2$—, wherein $R^9$ is hydrogen, halogen, hydroxy, nitro, cyano, formyl, $C_{1-12}$alkyl, $C_{1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR$^{13}$, or —SO$_2$R$^{14}$, wherein $R^{13}$ and $R^{14}$ independently of each other are selected from hydroxy, halogen, $C_{1-6}$alkoxy, amino optionally substituted with one or more $C_{1-6}$alkyl, perhalomethyl or aryl;

T is >N—, >CH—, >C<, —CH$_2$—N<,

Z is —CH$_2$—, ═CH—, >N—, —O—, —S—, >CO, >SO, >SO$_2$, >NR$^{11}$, wherein $R^{11}$ is hydrogen, halogen, hydroxy, nitro, cyano, formyl, $C_{1-12}$alkyl, $C_{1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR$^{15}$, or —SO$_2$R$^{16}$, wherein $R^{15}$ and $R^{16}$ independently of each other are selected from hydroxy, halogen, $C_{1-6}$alkoxy, amino optionally substituted with one or more $C_{1-6}$alkyl, perhalomethyl or aryl;

Q is —O—, —S—, >SO$_2$, >NR$^{12}$, wherein $R^{12}$ is hydrogen, hydroxy, nitro, cyano, formyl, $C_{1-12}$alkyl, $C_{1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, $C_{1-12}$alkylamino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR$^{17}$, or —SO$_2$R$^{18}$, wherein $R^{17}$ and $R^{18}$ independently of each other are selected from hydroxy, halogen, $C_{1-6}$alkoxy, amino optionally substituted with one or more $C_{1-6}$alkyl, perhalomethyl or aryl;

k is 1 or 2,

T═══(Z)$_p$ and T═══(CH)$_k$ independently of each other represents a single bond or a double bond, provided that both are not a double bond at the same time, Ar represents arylene, heteroarylene, or a divalent heterocyclic group optionally substituted with one or more $C_{1-6}$alkyl or aryl;

$R^5$ represents hydrogen, hydroxy, halogen, $C_{1-12}$alkoxy, $C_{1-12}$alkyl, $C_{4-12}$-alkenynyl, $C_{2-12}$-alkenyl, $C_{2-12}$- alkynyl or aralkyl; optionally substituted with one or more halogen, perhalomethyl, hydroxy, nitro or cyano; or $R^5$ forms a bond together with $R^6$, $R^6$ represents hydrogen, hydroxy, halogen, $C_{1-12}$alkoxy, $C_{1-12}$alkyl, $C_{4-12}$-alkenynyl, $C_{2-12}$-alkenyl, $C_{2-12}$-alkynyl, acyl or aralkyl; optionally substituted with one or more halogen, perhalomethyl, hydroxy, nitro or cyano; or $R^6$ forms a bond together with $R^5$, $R^7$ represents hydrogen, $C_{1-12}$alkyl, $C_{4-12}$-alkenynyl, $C_{2-12}$-alkenyl, $C_{2-12}$-alkynyl, aryl, aralkyl, $C_{1-12}$alkoxy$C_{1-12}$alkyl, $C_{1-12}$alkoxycarbonyl, aryloxycarbonyl, $C_{1-12}$alkylaminocarbonyl, arylaminocarbonyl, acyl, heterocyclyl, heteroaryl or heteroaralkyl groups; optionally substituted with one or more halogen, perhalomethyl, hydroxy, nitro or cyano;

$R^8$ represents hydrogen, $C_{1-12}$alkyl, $C_{4-12}$-alkenynyl, $C_{2-12}$-alkenyl, $C_{2-12}$-alkynyl, aryl, aralkyl, heterocyclyl, heteroaryl or heteroaralkyl groups; optionally substituted with one or more halogen, perhalomethyl, hydroxy, nitro or cyano;

Y represents oxygen, sulphur or $NR^{10}$, where $R^{10}$ represents hydrogen, $C_{1-12}$alkyl, aryl, hydroxy$C_{1-12}$alkyl or aralkyl groups or when Y is $NR^{10}$, $R^8$ and $R^{10}$ may form a 5 or 6 membered nitrogen containing ring, optionally substituted with one or more $C_{1-6}$alkyl;

n is an integer ranging from 0 to 3;

m is an integer ranging from 0 to 1;

p is an integer ranging from 0 to 1;

with the proviso that T is not N when p is 0;

or a pharmaceutically acceptable salt thereof.

In a preferred embodiment, the present invention is concerned with compounds of formula I wherein $R^1$, $R^2$, $R^3$, and $R^4$ independently of each other represent hydrogen, halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-7}$alkyl, amino, acylamino, $C_{1-7}$alkyl-amino, arylamino, aralkylamino, amino$C_{1-7}$alkyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino, aralkoxycarbonylamino, —$COR^{11}$, or —$SO_2R^{12}$, wherein $R^{11}$ and $R^{12}$ independently of each other are selected from hydroxy, perhalomethyl, $C_{1-6}$alkoxy or amino optionally substituted with one or more $C_{1-6}$alkyl, perhalomethyl or aryl; optionally substituted with one or more halogen, perhalomethyl, hydroxy, or cyano;

or $R^1$ and $R^2$, $R^2$ and $R^3$ and/or $R^3$ and $R^4$ may form a cyclic ring containing from 5 to 7 carbon atoms optionally substituted with one or more $C_{1-6}$alkyl.

In another preferred embodiment, the present invention is concerned with compounds of formula I wherein $R^1$, $R^2$, $R^3$, and $R^4$ independently of each other represent hydrogen, halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-7}$alkyl, amino, acylamino, $C_{1-7}$alkyl-amino, arylamino, aralkylamino, amino$C_{1-7}$alkyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino, aralkoxycarbonylamino.

In another preferred embodiment, the present invention is concerned with compounds of formula I wherein $R^1$, $R^2$, $R^3$, and $R^4$ independently of each other represent hydrogen, halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, acyl, hydroxy$C_{1-7}$alkyl, amino, acylamino, $C_{1-7}$alkyl-amino, arylamino, aralkylamino, $C_{1-7}$alkoxy$C_{1-7}$alkyl, aryloxy$C_{1-7}$alkyl, aralkoxy$C_{1-7}$alkyl, or $C_{1-7}$alkylthio.

In another preferred embodiment, the present invention is concerned with compounds of formula I wherein $R^1$, $R^2$, $R^3$, and $R^4$ independently of each other represent hydrogen, halogen, $C_{1-7}$alkyl, $C_{1-7}$alkoxy, aryl, or aryloxy.

In another preferred embodiment, the present invention is concerned with compounds of formula I wherein $R^1$, $R^2$, $R^3$, and $R^4$ independently of each other represent hydrogen, or $C_{1-7}$alkoxy.

In another preferred embodiment, the present invention is concerned with compounds of formula I wherein ring A represents a 5–6 membered cyclic ring, optionally substituted with one or more halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-7}$alkyl, amino, acylamino, $C_{1-7}$alkyl-amino, arylamino, aralkylamino, amino$C_{1-7}$alkyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino, aralkoxycarbonylamino, —$COR^{11}$, or —$SO_2R^{12}$, wherein $R^{11}$ and $R^{12}$ independently of each other are selected from hydroxy, perhalomethyl, or amino optionally substituted with one or more $C_{1-6}$alkyl, perhalomethyl or aryl; optionally substituted with one or more halogen, perhalomethyl, hydroxy, or cyano.

In another preferred embodiment, the present invention is concerned with compounds of formula I wherein ring A represents a 5–6 membered cyclic ring, optionally substituted with one or more halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, heterocyclyl, heteroaryl, heteroaralkyl, heteroaryloxy, heteroaralkoxy, acyl, amino, acylamino, $C_{1-7}$alkyl-amino, arylamino, aralkylamino, amino$C_{1-7}$alkyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl.

In another preferred embodiment, the present invention is concerned with compounds of formula I wherein ring A represents a 5–6 membered cyclic ring, optionally substituted with one or more halogen, hydroxy, cyano, or $C_{1-7}$alkyl, $C_{1-7}$alkoxy.

In another preferred embodiment, the present invention is concerned with compounds of formula I wherein X is a valence bond, —$(CHR^9)$—, —$(CHR^9)$—$CH_2$—, —$CH=CH$—, —O—, —O—$(CHR^9)$—, —S—$(CHR^9)$—, —$(NR^9)$—$CH_2$—, —$(CHR^9)$—$CH=CH$—, —$(CHR^9)$—$CH_2$—$CH_2$—, —$(C=O)$, —O—$CH_2$—O—, —$(NR^9)$—, —$(NR^9)$—$S(O_2)$—, —$CH=(CR^9)$—, —$(CO)$—$(CHR^9)$—, —$CH_2$—$(SO)$—, —S—, —$(SO)$—, —$(SO_2)$—, —$CH_2$—$(SO_2)$—, —$CH_2$—O—$CH_2$—, wherein $R^9$ is hydrogen, halogen, hydroxy, cyano, $C_{1-7}$alkyl, $C_{1-7}$alkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, $C_{1-7}$alkyl-amino, arylamino, aralkylamino, amino$C_{1-7}$alkyl, $C_{1-7}$alkoxycarbonyl, aryloxycarbonyl, aralkoxycarbonyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino, aralkoxycarbonylamino, —$COR^{13}$, or —$SO_2R^{14}$, wherein $R^{13}$ and $R^{14}$ independently of each other are selected from hydroxy, $C_{1-6}$alkoxy, amino optionally substituted with one or more $C_{1-6}$alkyl, perhalomethyl or aryl.

In another preferred embodiment, the present invention is concerned with compounds of formula I wherein X is a valence bond, —(CHR$^9$)—, —(CHR$^9$)—CH$_2$—, —CH=CH—, —O—, —O—(CHR$^9$)—, —S—(CHR$^9$)—, —(NR$^9$)—CH$_2$—, —(CHR$^9$)—CH=CH—, —(CHR$^9$)—CH$_2$—CH$_2$——(C=O)—, —O—CH$_2$—O—, —(NR$^9$)—, —(NR$^9$)—S(O$_2$)—, —CH=(CR$^9$)—, —(CO)—(CHR$^9$)—, —CH$_2$—(SO)—, —S—, —(SO)—, —(SO$_2$)—, —CH$_2$—(SO$_2$)—, —CH$_2$—O—CH$_2$—, wherein R$^9$ is hydrogen, halogen, hydroxy, C$_{1-7}$alkyl, C$_{1-7}$alkoxy, aryl.

In another preferred embodiment, the present invention is concerned with compounds of formula I wherein X is a valence bond, —(CHR$^9$)—, —(CHR$^9$)—CH$_2$—, —CH=CH—, —O—, —O—(CHR$^9$)—, —S—(CHR$^9$)—, —(NR$^9$)—CH$_2$—, —(C=O)—, —O—CH$_2$—O—, —(NR$^9$)—, —CH=(CR$^9$)—, —(CO)—(CHR$^9$)—, —CH$_2$—(SO)—, —S—, —(SO)—, —(SO$_2$)—, —CH$_2$—(SO$_2$)—, —CH$_2$—O—CH$_2$—, wherein R$^9$ is hydrogen, halogen, hydroxy, C$_{1-7}$alkyl, C$_{1-7}$alkoxy, aryl.

In another preferred embodiment, the present invention is concerned with compounds of formula I wherein T is >N—, >CH— or >C<.

In another preferred embodiment, the present invention is concerned with compounds of formula I wherein Z is —CH$_2$—, =CH—, >N—, —O—, —S—, >CO, >SO, >SO$_2$, >NR$^{11}$, wherein R$^{11}$ is hydrogen, C$_{1-7}$alkyl, aryl, aralkyl, heterocyclyl, heteroaryl, heteroaralkyl, acyl, acyloxy, hydroxyalkyl, aminoC$_{1-7}$alkyl, C$_{1-7}$alkoxycarbonyl, aryloxycarbonyl, aralkoxycarbonyl, C$_{1-7}$alkoxyC$_{1-7}$alkyl, aryloxyC$_{1-7}$alkyl, aralkoxyC$_{1-7}$alkyl, thioC$_{1-7}$alkyl, —COR$^{15}$, or —SO$_2$R$^{16}$, wherein R$^{15}$ and R$^{16}$ independently of each other are selected from hydroxy, C$_{1-6}$alkoxy, amino optionally substituted with one or more C$_{1-6}$alkyl, perhalomethyl or aryl.

In another preferred embodiment, the present invention is concerned with compounds of formula I wherein Z is —CH$_2$—, =CH—, >N—, —O—, —S—, >CO, >SO, >SO$_2$, >NR$^{11}$, wherein R$^{11}$ is hydrogen, C$_{1-7}$alkyl, aryl, aralkyl, heterocyclyl, heteroaryl, heteroaralkyl, acyl, acyloxy, hydroxyalkyl, C$_{1-7}$alkoxyC$_{1-7}$alkyl, aryloxyC$_{1-7}$alkyl, aralkoxyC$_{1-7}$alkyl.

In another preferred embodiment, the present invention is concerned with compounds of formula I wherein Z is —CH$_2$—, =CH—, >N—, —O—, —S—, >CO, >SO, >SO$_2$, >NR$^{11}$, wherein R$^{11}$ is hydrogen, C$_{1-7}$alkyl.

In another preferred embodiment, the present invention is concerned with compounds of formula I wherein Q is —O—, —S— or >NR$^{12}$, wherein R$^{12}$ is hydrogen, or methyl.

In another preferred embodiment, the present invention is concerned with compounds of formula I wherein Ar represents arylene optionally substituted with one or more C$_{1-6}$alkyl or aryl.

In another preferred embodiment, the present invention is concerned with compounds of formula I wherein Ar represents phenyl.

In another preferred embodiment, the present invention is concerned with compounds of formula I wherein R$^5$ represents hydrogen, hydroxy, halogen, C$_{1-7}$alkoxy, C$_{1-7}$alkyl, C$_{4-7}$-alkenynyl, C$_{2-7}$-alkenyl, C$_{2-7}$-alkynyl or aralkyl, or R$^5$ forms a bond together with R$^6$.

In another preferred embodiment, the present invention is concerned with compounds of formula I wherein R$^5$ represents hydrogen or R$^5$ forms a bond together with R$^6$.

In another preferred embodiment, the present invention is concerned with compounds of formula I wherein R$^6$ represents hydrogen, C$_{1-7}$alkoxy, C$_{1-7}$alkyl, C$_{4-7}$-alkenynyl, C$_{2-7}$-alkenyl, C$_{2-7}$-alkynyl, acyl or aralkyl, or R$^6$ forms a bond together with R$^5$.

In another preferred embodiment, the present invention is concerned with compounds of formula I wherein R$^6$ represents hydrogen or R$^6$ forms a bond together with R$^5$.

In another preferred embodiment, the present invention is concerned with compounds of formula I wherein R$^7$ represents hydrogen, C$_{1-7}$alkyl, C$_{4-7}$-alkenynyl, C$_{2-7}$-alkenyl, C$_{2-7}$-alkynyl, aryl, aralkyl, C$_{1-7}$alkoxyC$_{1-7}$alkyl, C$_{1-7}$alkoxycarbonyl, aryloxycarbonyl, C$_{1-7}$alkylaminocarbonyl, arylaminocarbonyl, acyl, heterocyclyl, heteroaryl or heteroaralkyl groups.

In another preferred embodiment, the present invention is concerned with compounds of formula I wherein R$^7$ represents hydrogen, C$_{1-7}$alkyl, C$_{4-7}$-alkenynyl, C$_{2-7}$-alkenyl or C$_{2-7}$-alkynyl.

In another preferred embodiment, the present invention is concerned with compounds of formula I wherein R$^7$ represents C$_{1-2}$alkyl.

In another preferred embodiment, the present invention is concerned with compounds of formula I wherein R$^8$ represents hydrogen, C$_{1-7}$alkyl, C$_{4-7}$-alkenynyl, C$_{2-7}$-alkenyl, C$_{2-7}$-alkynyl, aryl, aralkyl, heterocyclyl, heteroaryl or heteroaralkyl groups; optionally substituted with one or more halogen, perhalomethyl, hydroxy, nitro or cyano.

In another preferred embodiment, the present invention is concerned with compounds of formula I wherein R$^8$ represents hydrogen, C$_{1-7}$alkyl, C$_{4-7}$-alkenynyl, C$_{2-7}$-alkenyl, C$_{2-7}$-alkynyl, aryl or aralkyl.

In another preferred embodiment, the present invention is concerned with compounds of formula I wherein R$^8$ represents hydrogen or C$_{1-2}$alkyl.

In another preferred embodiment, the present invention is concerned with compounds of formula I wherein Y represents oxygen, sulphur or NR$^{10}$, where R$^{10}$ represents hydrogen, C$_{1-7}$alkyl, aryl, hydroxyC$_{1-7}$alkyl or aralkyl groups.

In another preferred embodiment, the present invention is concerned with compounds of formula I wherein Y represents oxygen.

In another preferred embodiment, the present invention is concerned with compounds of formula I wherein A is benzo.

In another preferred embodiment, the present invention is concerned with compounds of formula I wherein X is —O—.

In another preferred embodiment, the present invention is concerned with compounds of formula I wherein X is —S—.

In another preferred embodiment, the present invention is concerned with compounds of formula I wherein X is —(CHR$^9$)—CH$_2$—, wherein R$^9$ is H.

In another preferred embodiment, the present invention is concerned with compounds of formula I wherein X is —O—(CHR$^9$)—, wherein R$^9$ is H.

In another preferred embodiment, the present invention is concerned with compounds of formula I wherein X is —S—(CHR$^9$)—, wherein R$^9$ is H.

In another preferred embodiment, the present invention is concerned with compounds of formula I wherein X is —(NR$^9$)—CH$_2$, wherein R$^9$ is C$_{1-12}$-alkyl, preferably methyl.

In another preferred embodiment, the present invention is concerned with compounds of formula I wherein X is —O—(CHR$^9$)—, wherein R$^9$ is H.

In another preferred embodiment, the present invention is concerned with compounds of formula I wherein X is —(C=O)—.

In another preferred embodiment, the present invention is concerned with compounds of formula I wherein X is —(CHR$^9$)—, wherein R$^9$ is H.

In another preferred embodiment, the present invention is concerned with compounds of formula I wherein X is —(CHR$^9$)—CH$_2$—CH$_2$—, wherein R$^9$ is H.

In another preferred embodiment, the present invention is concerned with compounds of formula I wherein X is a valence bond.

In another preferred embodiment, the present invention is concerned with compounds of formula I wherein R$^1$, R$^2$, R$^3$ and R$^4$ are H.

In another preferred embodiment, the present invention is concerned with compounds of formula I wherein n is 1.

In another preferred embodiment, the present invention is concerned with compounds of formula I wherein n is 2.

In another preferred embodiment, the present invention is concerned with compounds of formula I wherein m is 1.

In another preferred embodiment, the present invention is concerned with compounds of formula I wherein k is 0.

In another preferred embodiment, the present invention is concerned with compounds of formula I wherein k is 1.

In another preferred embodiment, the present invention is concerned with compounds of formula I wherein Q is —O—.

In another preferred embodiment, the present invention is concerned with compounds of formula I wherein T═(CH)$_k$ represents a single bond or a double bond.

In another preferred embodiment, the present invention is concerned with compounds of formula I wherein T is >CH— or >C<.

In another preferred embodiment, the present invention is concerned with compounds of formula I wherein T is >N— and p is 1.

In another preferred embodiment, the present invention is concerned with compounds of formula I wherein Z is —CH$_2$— or >CO and p is 1.

In another preferred embodiment, the present invention is concerned with compounds of formula I wherein R$^5$ is H.

In another preferred embodiment, the present invention is concerned with compounds of formula I wherein R$^6$ is H.

In another preferred embodiment, the present invention is concerned with compounds of formula I wherein R$^7$ is ethyl.

In another preferred embodiment, the present invention is concerned with compounds of formula I wherein R$^8$ is H.

In another preferred embodiment, the present invention is concerned with compounds of formula I wherein R$^8$ is ethyl.

In another preferred embodiment, the present invention is concerned with compounds of formula I wherein Z is —S— and T is >CH—.

In another preferred embodiment, the present invention is concerned with compounds of formula I wherein Z is —O— and T is >CH—.

In another preferred embodiment, the present invention is concerned with compounds of formula I wherein Ar is phenylene.

In another preferred embodiment, the present invention is concerned with compounds of formula I wherein p is 0.

Preferred compounds of the invention are:

2-Ethoxy-3-[4-(2-xanthen-9-ylidene-ethoxy)-phenyl]-propionic acid,
2-Methoxy-3-[4-(2-xanthen-9-ylidene-ethoxy)-phenyl]-propionic acid,
2-Ethoxy-3-[4-(2-xanthen-9-ylidene-propoxy)-phenyl]-propionic acid,
2-Ethoxy-3-[4-(2-thioxanthen-9-ylidene-ethoxy)-phenyl]-propionic acid,
2-Methoxy-3-[4-(2-thioxanthen-9-ylidene-ethoxy)-phenyl]-propionic acid,
2-Ethoxy-3-[4-(2-thioxanthen-9-ylidene-propoxy)-phenyl]-propionic acid,
2-Ethoxy-3-{4-[2-(9H-thioxanthen-9-yl)-ethoxy]-phenyl}-propionic acid,
3-{4-[2-(10,11-Dihydro-dibenzo[a,d]cyclohepten-5-ylidene)-ethoxy]-phenyl}-2-ethoxy-propionic acid,
3-{4-[2-(10,11-Dihydro-dibenzo[a,d]cyclohepten-5-ylidene)-propoxy]-phenyl}-2-ethoxy-propionic acid,
3-{4-[2-(6H-Dibenzo[b,e]oxepin-11-ylidene)-ethoxy]-phenyl}-2-ethoxy-propionic acid,
2-Ethoxy-3-{4-[2-(11H-10-thia-dibenzo[a,d]cyclohepten-5-ylidene)-ethoxy]-phenyl}-propionic acid,
3-{4-[2-(5,11-Dihydro-10-thia-dibenzo[a,d]cyclohepten-5-yl)-ethoxy]-phenyl}-2-ethoxy-propionic acid,
2-Ethoxy-3-{4-[2-(5-methyl-5,6-dihydro-dibenzo[b,e]azepin-11-ylidene)-ethoxy]-phenyl}-propionic acid,
2-Ethoxy-3-{4-[2-(11-oxo-6,11-dihydro-dibenzo[b,e]azepin-5-yl)-ethoxy]-phenyl}-propionic acid,
3-{4-[2-(6,11-Dihydro-dibenzo[b,e]azepin-5-yl)-ethoxy]-phenyl}-2-ethoxy-propionic acid,
3-{4-[2-(6,11-Dioxo-6,11-dihydro-dibenzo[b,e]azepin-5-yl)-ethoxy]-phenyl}-2-ethoxy-propionic acid,
3-{4-[2-(11H-Dibenzo[b,f][1,4]oxazepin-10-yl)-ethoxy]-phenyl}-2-ethoxy-propionic acid,
3-{4-[2-(11,12-Dihydro-dibenzo[a,e]cycloocten-5-yl)-ethoxy]-phenyl}-2-ethoxy-propionic acid,
Ethyl 2-ethoxy-3-[4-(2-fluoren-9-ylidene-ethoxy)-phenyl]-propionate,
Propyl 2-ethoxy-3-[4-(2-fluoren-9-ylidene-ethoxy)-phenyl]-propionate,
Butyl 2-ethoxy-3-[4-(2-fluoren-9-ylidene-ethoxy)-phenyl]-propionate,
Pentyl 2-ethoxy-3-[4-(2-fluoren-9-ylidene-ethoxy)-phenyl]-propionate,
Hexyl 2-ethoxy-3-[4-(2-fluoren-9-ylidene-ethoxy)-phenyl]-propionate,
Heptyl 2-ethoxy-3-[4-(2-fluoren-9-ylidene-ethoxy)-phenyl]-propionate,
N,N-Dimethyl 2-ethoxy-3-[4-(2-fluoren-9-ylidene-ethoxy)-phenyl]-propionamide,
N-Methyl 2-ethoxy-3-[4-(2-fluoren-9-ylidene-ethoxy)-phenyl]-propionamide,
N,N-Diethyl 2-ethoxy-3-[4-(2-fluoren-9-ylidene-ethoxy)-phenyl]-propionamide,
N-Ethyl 2-ethoxy-3-[4-(2-fluoren-9-ylidene-ethoxy)-phenyl]-propionamide,
N-Benzyl 2-ethoxy-3-[4-(2-fluoren-9-ylidene-ethoxy)-phenyl]-propionamide,
N-Propyl 2-ethoxy-3-[4-(2-fluoren-9-ylidene-ethoxy)-phenyl]-propionamide,
Ethyl 3-[4-(2-fluoren-9-ylidene-ethoxy)-phenyl]-2-methoxy-propionate,
Ethyl 3-[4-(2-fluoren-9-ylidene-ethoxy)-phenyl]-2-propoxy-propionate,
Ethyl 2-butoxy-3-[4-(2-fluoren-9-ylidene-ethoxy)-phenyl]-propionate,
Ethyl 3-[4-(2-fluoren-9-ylidene-ethoxy)-phenyl]-2-pentyloxy-propionate,
Ethyl 3-[4-(2-fluoren-9-ylidene-ethoxy)-phenyl]-2-hexyloxy-propionate,
Ethyl 3-[4-(2-fluoren-9-ylidene-ethoxy)-phenyl]-2-heptyloxy-propionate,
Ethyl 3-[4-(3-fluoren-9-ylidene-propoxy)-phenyl]-2-methoxy-propionate,
Ethyl 2-ethoxy-3-[4-(3-fluoren-9-ylidene-propoxy)-phenyl]-propionate, Ethyl 3-[4-(3-fluoren-9-ylidene-propoxy)-phenyl]-2-propoxy-propionate,
Ethyl 2-butoxy-3-[4-(3-fluoren-9-ylidene-propoxy)-phenyl]-propionate,
Ethyl 3-[4-(3-fluoren-9-ylidene-propoxy)-phenyl]-2-pentyloxy-propionate,
Ethyl 3-[4-(3-fluoren-9-ylidene-propoxy)-phenyl]-2-hexyloxy-propionate,
Ethyl 3-[4-(3-fluoren-9-ylidene-propoxy)-phenyl]-2-heptyloxy-propionate,
Ethyl 3-[4-(4-fluoren-9-ylidene-butoxy)-phenyl]-2-methoxy-propionate,
Ethyl 2-ethoxy-3-[4-(4-fluoren-9-ylidene-butoxy)-phenyl]-propionate,
Ethyl 3-[4-(4-fluoren-9-ylidene-butoxy)-phenyl]-2-propoxy-propionate,
Ethyl 2-butoxy-3-[4-(4-fluoren-9-ylidene-butoxy)-phenyl]-propionate,
Ethyl 3-[4-(4-fluoren-9-ylidene-butoxy)-phenyl]-2-pentyloxy-propionate,
Ethyl 3-[4-(4-fluoren-9-ylidene-butoxy)-phenyl]-2-hexyloxy-propionate,
Ethyl 3-[4-(4-fluoren-9-ylidene-butoxy)-phenyl]-2-heptyloxy-propionate,
Ethyl 2-ethoxy-3-[4-(2-{2-methoxy-fluoren-9-ylidene}-ethoxy)-phenyl]-propionate,
Ethyl 2-ethoxy-3-[4-(2-{2-propoxy-fluoren-9-ylidene}-ethoxy)-phenyl]-propionate,
Ethyl 3-[4-(2-{2-butoxy-fluoren-9-ylidene}-ethoxy)-phenyl]-2-ethoxy-propionate,
Ethyl 2-ethoxy-3-[4-(2-{2-methyl-fluoren-9-ylidene}-ethoxy)-phenyl]-propionate,
Ethyl 3-[4-(2-{2-butyl-fluoren-9-ylidene}-ethoxy)-phenyl]-2-ethoxy-propionate,
Ethyl 2-ethoxy-3-[4-(2-{3-methoxy-fluoren-9-ylidene}-ethoxy)-phenyl]-propionate,
Ethyl 2-ethoxy-3-[4-(2-{3-propoxy-fluoren-9-ylidene}-ethoxy)-phenyl]-propionate,
Ethyl 3-[4-(2-{3-butoxy-fluoren-9-ylidene}-ethoxy)-phenyl]-2-ethoxy-propionate,
Ethyl 2-ethoxy-3-[4-(2-{3-methyl-fluoren-9-ylidene}-ethoxy)-phenyl]-propionate,
Ethyl 3-[4-(2-{3-butyl-fluoren-9-ylidene}-ethoxy)-phenyl]-2-ethoxy-propionate,
Ethyl 2-ethoxy-3-[4-(2-{4-methoxy-fluoren-9-ylidene}-ethoxy)-phenyl]-propionate,
Ethyl 2-ethoxy-3-[4-(2-{4-propoxy-fluoren-9-ylidene}-ethoxy)-phenyl]-propionate,
Ethyl 3-[4-(2-{4-butoxy-fluoren-9-ylidene}-ethoxy)-phenyl]-2-ethoxy-propionate,
Ethyl 2-ethoxy-3-[4-(2-{4-methyl-fluoren-9-ylidene}-ethoxy)-phenyl]-propionate,
Ethyl 3-[4-(2-{4-butyl-fluoren-9-ylidene}-ethoxy)-phenyl]-2-ethoxy-propionate,
Ethyl 2-ethoxy-3-[4-(2-{3,6-Dimethoxy-fluoren-9-ylidene}-ethoxy)-phenyl]-propionate,
Ethyl 2-ethoxy-3-[4-(2-{2,7-Dimethoxy-fluoren-9-ylidene}-ethoxy)-phenyl]-propionate,
Ethyl 2-ethoxy-3-[4-(2-{4,5-Dimethoxy-fluoren-9-ylidene}-ethoxy)-phenyl]-propionate,
Ethyl 2-ethoxy-3-[4-(2-{3,6-Dimethyl-fluoren-9-ylidene}-ethoxy)-phenyl]-propionate,
Ethyl 2-ethoxy-3-[4-(2-{2,7-Dimethyl-fluoren-9-ylidene}-ethoxy)-phenyl]-propionate,
Ethyl 2-ethoxy-3-[4-(2-{4,5-Dimethyl-fluoren-9-ylidene}-ethoxy)-phenyl]-propionate,
3-[4-(2-Fluoren-9-ylidene-ethoxy)-phenyl]-2-methoxy-propionic acid,
2-Ethoxy-3-[4-(2-fluoren-9-ylidene-ethoxy)-phenyl]-propionic acid,
3-[4-(2-Fluoren-9-ylidene-ethoxy)-phenyl]-2-propoxy-propionic acid,
2-Butoxy-3-[4-(2-fluoren-9-ylidene-ethoxy)-phenyl]-propionic acid,
3-[4-(2-Fluoren-9-ylidene-ethoxy)-phenyl]-2-pentyloxy-propionic acid,
3-[4-(2-Fluoren-9-ylidene-ethoxy)-phenyl]-2-hexyloxy-propionic acid,
3-[4-(2-Fluoren-9-ylidene-ethoxy)-phenyl]-2-heptyloxy-propionic acid,
3-[4-(3-Fluoren-9-ylidene-propoxy)-phenyl]-2-methoxy-propionic acid,
2-Ethoxy-3-[4-(3-fluoren-9-ylidene-propoxy)-phenyl]-propionic acid,
3-[4-(3-Fluoren-9-ylidene-propoxy)-phenyl]-2-propoxy-propionic acid,
2-Butoxy-3-[4-(3-fluoren-9-ylidene-propoxy)-phenyl]-propionic acid,
3-[4-(3-Fluoren-9-ylidene-propoxy)-phenyl]-2-pentyloxy-propionic acid,
3-[4-(3-Fluoren-9-ylidene-propoxy)-phenyl]-2-hexyloxy-propionic acid,
3-[4-(3-Fluoren-9-ylidene-propoxy)-phenyl]-2-heptyloxy-propionic acid,
3-[4-(4-Fluoren-9-ylidene-butoxy)-phenyl]-2-methoxy-propionic acid,
2-Ethoxy-3-[4-(4-fluoren-9-ylidene-butoxy)-phenyl]-propionic acid,
3-[4-(4-Fluoren-9-ylidene-butoxy)-phenyl]-2-propoxy-propionic acid
2-Butoxy-3-[4-(4-fluoren-9-ylidene-butoxy)-phenyl]-propionic acid,
3-[4-(4-Fluoren-9-ylidene-butoxy)-phenyl]-2-pentyloxy-propionic acid,
3-[4-(4-Fluoren-9-ylidene-butoxy)-phenyl]-2-hexyloxy-propionic acid,
3-[4-(4-Fluoren-9-ylidene-butoxy)-phenyl]-2-heptyloxy-propionic acid,
2-Ethoxy-3-[4-(2-{2-methoxy-fluoren-9-ylidene}-ethoxy)-phenyl]-propionic acid,
2-Ethoxy-3-[4-(2-{2-propoxy-fluoren-9-ylidene}-ethoxy)-phenyl]-propionic acid,
3-[4-(2-{2-Butoxy-fluoren-9-ylidene}-ethoxy)-phenyl]-2-ethoxy-propionic acid,
2-Ethoxy-3-[4-(2-{2-methyl-fluoren-9-ylidene}-ethoxy)-phenyl]-propionic acid,
3-[4-(2-{2-Butyl-fluoren-9-ylidene}-ethoxy)-phenyl]-2-ethoxy-propionic acid,
2-Ethoxy-3-[4-(2-{3-methoxy-fluoren-9-ylidene}-ethoxy)-phenyl]-propionic acid,
2-Ethoxy-3-[4-(2-{3-propoxy-fluoren-9-ylidene}-ethoxy)-phenyl]-propionic acid,
3-[4-(2-{3-Butoxy-fluoren-9-ylidene}-ethoxy)-phenyl]-2-ethoxy-propionic acid,
2-Ethoxy-3-[4-(2-{3-methyl-fluoren-9-ylidene}-ethoxy)-phenyl]-propionic acid,
3-[4-(2-{3-Butyl-fluoren-9-ylidene}-ethoxy)-phenyl]-2-ethoxy-propionic acid,
2-Ethoxy-3-[4-(2-{4-methoxy-fluoren-9-ylidene}-ethoxy)-phenyl]-propionic acid,
2-Ethoxy-3-[4-(2-{4-propoxy-fluoren-9-ylidene}-ethoxy)-phenyl]-propionic acid,
3-[4-(2-{4-Butoxy-fluoren-9-ylidene}-ethoxy)-phenyl]-2-ethoxy-propionic acid,
2-Ethoxy-3-[4-(2-{4-methyl-fluoren-9-ylidene}-ethoxy)-phenyl]-propionic acid, 3-[4-(2-{4-Butyl-fluoren-9-ylidene}-ethoxy)-phenyl]-2-ethoxy-propionic acid,
2-Ethoxy-3-[4-(2-{3,6-Dimethoxy-fluoren-9-ylidene}-ethoxy)-phenyl]-propionic acid,
2-Ethoxy-3-[4-(2-{2,7-Dimethoxy-fluoren-9-ylidene}-ethoxy)-phenyl]-propionic acid,
2-Ethoxy-3-[4-(2-{4,5-Dimethoxy-fluoren-9-ylidene}-ethoxy)-phenyl]-propionic acid,
2-Ethoxy-3-[4-(2-{3,6-Dimethyl-fluoren-9-ylidene}-ethoxy)-phenyl]-propionic acid,
2-Ethoxy-3-[4-(2-{2,7-Dimethyl-fluoren-9-ylidene}-ethoxy)-phenyl]-propionic acid,
2-Ethoxy-3-[4-(2-{4,5-Dimethyl-fluoren-9-ylidene}-ethoxy)-phenyl]-propionic acid,
Ethyl 3-{4-[2-(6H-dibenzo[b,e]oxepin-11-ylidene)-ethoxy]-phenyl}-2-ethoxy-propionate,
Ethyl 3-{4-[3-(6H-dibenzo[b,e]oxepin-11-ylidene)-propoxy]-phenyl}-2-ethoxy-propionate,
Ethyl 3-{4-[4-(6H-dibenzo[b,e]oxepin-11-ylidene)-butoxy]-phenyl}-2-ethoxy-propionate,
3-{4-[3-(6H-Dibenzo[b,e]oxepin-11-ylidene)-propoxy]-phenyl}-2-ethoxy-propionic acid,
3-{4-[4-(6H-Dibenzo[b,e]oxepin-11-ylidene)-butoxy]-phenyl}-2-ethoxy-propionic acid,
Ethyl 3-{4-[2-(6H-dibenzo[b,e]oxepin-11-ylidene)-ethoxy]-phenyl}-2-methoxy-propionate,
Ethyl 3-{4-[3-(6H-dibenzo[b,e]oxepin-11-ylidene)-propoxy]-phenyl}-2-methoxy-propionate,
Ethyl 3-{4-[4-(6H-dibenzo[b,e]oxepin-11-ylidene)-butoxy]-phenyl}-2-methoxy-propionate,
3-{4-[2-(6H-Dibenzo[b,e]oxepin-11-ylidene)-ethoxy]-phenyl}-2-methoxy-propionic acid,
3-{4-[3-(6H-Dibenzo[b,e]oxepin-11-ylidene)-propoxy]-phenyl}-2-methoxy-propionic acid,
3-{4-[4-(6H-Dibenzo[b,e]oxepin-11-ylidene)-butoxy]-phenyl}-2-methoxy-propionic acid,
Ethyl 3-{4-[2-(6H-dibenzo[b,e]oxepin-11-ylidene)-ethoxy]-phenyl}-2-propoxy-propionate,
Ethyl 3-{4-[3-(6H-dibenzo[b,e]oxepin-11-ylidene)-propoxy]-phenyl}-2-propoxy-propionate,
Ethyl 3-{4-[4-(6H-dibenzo[b,e]oxepin-11-ylidene)-butoxy]-phenyl}-2-propoxy-propionate,
3-{4-[2-(6H-Dibenzo[b,e]oxepin-11-ylidene)-ethoxy]-phenyl}-2-propoxy-propionic acid,
3-{4-[3-(6H-Dibenzo[b,e]oxepin-11-ylidene)-propoxy]-phenyl}-2-propoxy-propionic acid,
3-{4-[4-(6H-Dibenzo[b,e]oxepin-11-ylidene)-butoxy]-phenyl}-2-propoxy-propionic acid,
Ethyl 2-ethoxy-3-[4-(2-(9H-fluoren-9-yl)-ethoxy)-phenyl]-propionate,
Propyl 2-ethoxy-3-[4-(2-(9H-fluoren-9-yl)-ethoxy)-phenyl]-propionate,
Butyl 2-ethoxy-3-[4-(2-(9H-fluoren-9-yl)-ethoxy)-phenyl]-propionate,
Pentyl 2-ethoxy-3-[4-(2-(9H-fluoren-9-yl)-ethoxy)-phenyl]-propionate,
Hexyl 2-ethoxy-3-[4-(2-(9H-fluoren-9-yl)-ethoxy)-phenyl]-propionate,
Heptyl 2-ethoxy-3-[4-(2-(9H-fluoren-9-yl)-ethoxy)-phenyl]-propionate,
N,N-Dimethyl 2-ethoxy-3-[4-(2-(9H-fluoren-9-yl)-ethoxy)-phenyl]-propionamide,
N-Methyl 2-ethoxy-3-[4-(2-(9H-fluoren-9-yl)-ethoxy)-phenyl]-propionamide,
N,N-Diethyl 2-ethoxy-3-[4-(2-(9H-fluoren-9-yl)-ethoxy)-phenyl]-propionamide,
N-Ethyl 2-ethoxy-3-[4-(2-(9H-fluoren-9-yl)-ethoxy)-phenyl]-propionamide,
N-Benzyl 2-ethoxy-3-[4-(2-(9H-fluoren-9-yl)-ethoxy)-phenyl]-propionamide,
N-Propyl 2-ethoxy-3-[4-(2-(9H-fluoren-9-yl)-ethoxy)-phenyl]-propionamide,
Ethyl 3-[4-(2-(9H-fluoren-9-yl)-ethoxy)-phenyl]-2-methoxy-propionate,
Ethyl 3-[4-(2-(9H-fluoren-9-yl)-ethoxy)-phenyl]-2-propoxy-propionate,
Ethyl 2-butoxy-3-[4-(2-(9H-fluoren-9-yl)-ethoxy)-phenyl]-propionate,
Ethyl 3-[4-(2-(9H-fluoren-9-yl)-ethoxy)-phenyl]-2-pentyloxy-propionate,
Ethyl 3-[4-(2-(9H-fluoren-9-yl)-ethoxy)-phenyl]-2-hexyloxy-propionate,
Ethyl 3-[4-(2-(9H-fluoren-9-yl)-ethoxy)-phenyl]-2-heptyloxy-propionate,
Ethyl 3-[4-(3-(9H-fluoren-9-yl)-propoxy)-phenyl]-2-methoxy-propionate,
Ethyl 2-ethoxy-3-[4-(3-(9H-fluoren-9-yl)-propoxy)-phenyl]-propionate,
Ethyl 3-[4-(3-(9H-fluoren-9-yl)-propoxy)-phenyl]-2-propoxy-propionate,
Ethyl 2-butoxy-3-[4-(3-(9H-fluoren-9-yl)-propoxy)-phenyl]-propionate,
Ethyl 3-[4-(3-(9H-fluoren-9-yl)-propoxy)-phenyl]-2-pentyloxy-propionate,
Ethyl 3-[4-(3-(9H-fluoren-9-yl)-propoxy)-phenyl]-2-hexyloxy-propionate,
Ethyl 3-[4-(3-(9H-fluoren-9-yl)-propoxy)-phenyl]-2-heptyloxy-propionate,
Ethyl 3-[4-(4-(9H-fluoren-9-yl)-butoxy)-phenyl]-2-methoxy-propionate,
Ethyl 2-ethoxy-3-[4-(4-(9H-fluoren-9-yl)-butoxy)-phenyl]-propionate,
Ethyl 3-[4-(4-(9H-fluoren-9-yl)-butoxy)-phenyl]-2-propoxy-propionate,
Ethyl 2-butoxy-3-[4-(4-(9H-fluoren-9-yl)-butoxy)-phenyl]-propionate,
Ethyl 3-[4-(4-(9H-fluoren-9-yl)-butoxy)-phenyl]-2-pentyloxy-propionate,
Ethyl 3-[4-(4-(9H-fluoren-9-yl)-butoxy)-phenyl]-2-hexyloxy-propionate,
Ethyl 3-[4-(4-(9H-fluoren-9-yl)-butoxy)-phenyl]-2-heptyloxy-propionate,
Ethyl 2-ethoxy-3-[4-(2-{9H-2-methoxy-fluoren-9-yl)}-ethoxy)-phenyl]-propionate,
Ethyl 2-ethoxy-3-[4-(2-{9H-2-propoxy-fluoren-9-yl)}-ethoxy)-phenyl]-propionate,
Ethyl 3-[4-(2-(9H-2-butoxyfluoren-9-yl)-ethoxy)-phenyl]-2-ethoxy-propionate,
Ethyl 2-ethoxy-3-[4-(2-(9H-2-methylfluoren-9-yl)-ethoxy)-phenyl]-propionate,
Ethyl 3-[4-(2-(9H-2-butylfluoren-9-yl)-ethoxy)-phenyl]-2-ethoxy-propionate,
Ethyl 2-ethoxy-3-[4-(2-(9H-3-methoxyfluoren-9-yl)-ethoxy)-phenyl]-propionate,
Ethyl 2-ethoxy-3-[4-(2-(9H-3-propoxyfluoren-9-yl)-ethoxy)-phenyl]-propionate,
Ethyl 3-[4-(2-(9H-3-butoxyfluoren-9-yl)-ethoxy)-phenyl]-2-ethoxy-propionate,
Ethyl 2-ethoxy-3-[4-(2-(9H-3-methylfluoren-9-yl)-ethoxy)-phenyl]-propionate,
Ethyl 3-[4-(2-(9H-3-butylfluoren-9-yl)-ethoxy)-phenyl]-2-ethoxy-propionate,
Ethyl 2-ethoxy-3-[4-(2-(9H-4-methoxyfluoren-9-yl)-ethoxy)-phenyl]-propionate,
Ethyl 2-ethoxy-3-[4-(2-(9H-4-propoxyfluoren-9-yl)-ethoxy)-phenyl]-propionate, Ethyl 3-[4-(2-(9H-4-butoxyfluoren-9-yl)-ethoxy)-phenyl]-2-ethoxy-propionate,
Ethyl 2-ethoxy-3-[4-(2-(9H-4-methylfluoren-9-yl)-ethoxy)-phenyl]-propionate,
Ethyl 3-[4-(2-(9H-4-butylfluoren-9-yl)-ethoxy)-phenyl]-2-ethoxy-propionate,
Ethyl 2-ethoxy-3-[4-(2-(9H-3,6dimethoxyfluoren-9-yl)-ethoxy)-phenyl]-propionate,
Ethyl 2-ethoxy-3-[4-(2-(9H-2,7-dimethoxyfluoren-9-yl)-ethoxy)-phenyl]-propionate,
Ethyl 2-ethoxy-3-[4-(2-(9H-4,5-dimethoxyfluoren-9-yl)-ethoxy)-phenyl]-propionate,
Ethyl 2-ethoxy-3-[4-(2-(9H-3,6-dimethyfluoren-9-yl)-ethoxy)-phenyl]-propionate,
Ethyl 2-ethoxy-3-[4-(2-(9H-2,7-dimethylfluoren-9-yl)-ethoxy)-phenyl]-propionate,
Ethyl 2-ethoxy-3-[4-(2-(9H-4,5-dimethylfluoren-9-yl)-ethoxy)-phenyl]-propionate,
3-[4-(2-(9H-Fluoren-9-yl)-ethoxy)-phenyl]-2-methoxy-propionic acid,
2-Ethoxy-3-[4-(2-(9H-Fluoren-9-yl)-ethoxy)-phenyl]-propionic acid,
3-[4-(2-(9H-Fluoren-9-yl)-ethoxy)-phenyl]-2-propoxy-propionic acid,
2-Butoxy-3-[4-(2-(9H-fluoren-9-yl)-ethoxy)-phenyl]-propionic acid,
3-[4-(2-(9H-Fluoren-9-yl)-ethoxy)-phenyl]-2-pentyloxy-propionic acid,
3-[4-(2-(9H-Fluoren-9yl)-ethoxy)-phenyl]-2-hexyloxy-propionic acid,
3-[4-(2-(9H-Fluoren-9-yl)-ethoxy)-phenyl]-2-heptyloxy-propionic acid,
3-[4-(3-(9H-Fluoren-9-yl)-propoxy)-phenyl]-2-methoxy-propionic acid,
2-Ethoxy-3-[4-(3-(9H-fluoren-9-yl)-propoxy)-phenyl]-propionic acid,
3-[4-(3-(9H-Fluoren-9-yl)-propoxy)-phenyl]-2-propoxy-propionic acid,
2-Butoxy-3-[4-(3-(9H-fluoren-9-yl)-propoxy)-phenyl]-propionic acid,
3-[4-(3-(9H-Fluoren-9-yl)-propoxy)-phenyl]-2-pentyloxy-propionic acid,
3-[4-(3-(9H-Fluoren-9-yl)-propoxy)-phenyl]-2-hexyloxy-propionic acid,
3-[4-(3-(9H-Fluoren-9-yl)-propoxy)-phenyl]-2-heptyloxy-propionic acid,
3-[4-(4-(9H-Fluoren-9-yl)-butoxy)-phenyl]-2-methoxy-propionic acid,
2-Ethoxy-3-[4-(4-(9H-fluoren-9-yl)-butoxy)-phenyl]-propionic acid,
3-[4-(4-(9H-Fluoren-9-yl)-butoxy)-phenyl]-2-propoxy-propionic acid,
2-Butoxy-3-[4-(4-(9H-fluoren-9-yl)-butoxy)-phenyl]-propionic acid,
3-[4-(4-(9H-Fluoren-9-yl)-butoxy)-phenyl]-2-pentyloxy-propionic acid,
3-[4-(4-(9H-Fluoren-9-yl)-butoxy)-phenyl]-2-hexyloxy-propionic acid,
3-[4-(4-(9H-Fluoren-9-yl)-butoxy)-phenyl]-2-heptyloxy-propionic acid,
2-Ethoxy-3-[4-(2-(9H-2-methoxyfluoren-9-yl)-ethoxy)-phenyl]-propionic acid,
2-Ethoxy-3-[4-(2-(9H-2-propoxyfluoren-9-yl)-ethoxy)-phenyl]-propionic acid,
3-[4-(2-(9H-2-Butoxyfluoren-9-yl)-ethoxy)-phenyl]-2-ethoxy-propionic acid,
2-Ethoxy-3-[4-(2-(9H-2-methylfluoren-9-yl)-ethoxy)-phenyl]-propionic acid,
3-[4-(2-(9H-2-Butylfluoren-9-yl)-ethoxy)-phenyl]-2-ethoxy-propionic acid,
2-Ethoxy-3-[4-(2-(9H-3-methoxyfluoren-9-yl)-ethoxy)-phenyl]-propionic acid,
2-Ethoxy-3-[4-(2-(9H-3-propoxyfluoren-9-yl)-ethoxy)-phenyl]-propionic acid,
3-[4-(2-(9H-3-Butoxyfluoren-9-yl)-ethoxy)-phenyl]-2-ethoxy-propionic acid,
2-Ethoxy-3-[4-(2-(9H-3-methylfluoren-9-yl)-ethoxy)-phenyl]-propionic acid,
3-[4-(2-(9H-3-Butylfluoren-9-yl)-ethoxy)-phenyl]-2-ethoxy-propionic acid,
2-Ethoxy-3-[4-(2-(9H-4-methoxyfluoren-9-yl)-ethoxy)-phenyl]-propionic acid,
2-Ethoxy-3-[4-(2-(9H-4-propoxyfluoren-9-yl)-ethoxy)-phenyl]-propionic acid,
3-[4-(2-( 9H-4-Butoxyfluoren-9-yl)-ethoxy)-phenyl]-2-ethoxy-propionic acid,
2-Ethoxy-3-[4-(2-(9H-4-methylfluoren-9-yl)-ethoxy)-phenyl]-propionic acid,
3-[4-(2-(9H-4-Butylfluoren-9-yl)-ethoxy)-phenyl]-2-ethoxy-propionic acid,
2-Ethoxy-3-[4-(2-(9H-3,6-dimethoxyfluoren-9-yl)-ethoxy)-phenyl]-propionic acid,
2-Ethoxy-3-[4-(2-(9H-2,7-dimethoxyfluoren-9-yl)-ethoxy)-phenyl]-propionic acid,
2-Ethoxy-3-[4-(2-(9H-4,5-dimethoxyfluoren-9-yl)-ethoxy)-phenyl]-propionic acid,
2-Ethoxy-3-[4-(2-(9H-3,6-dimethylfluoren-9-yl)-ethoxy)-phenyl]-propionic acid,
2-Ethoxy-3-[4-(2-(9H-2,7-dimethylfluoren-9-yl)-ethoxy)-phenyl]-propionic acid,
2-Ethoxy-3-[4-(2-(9H-4,5-dimethylfluoren-9-yl)-ethoxy)-phenyl]-propionic acid,
Ethyl 3-{4-[2-(10,11-dihydro-dibenzo[a,d]cyclohepten-5-ylidene)-ethoxy]-phenyl}-2-ethoxy-propionate,
Ethyl 3-{4-[3-(10,11-dihydro-dibenzo[a,d]cyclohepten-5-ylidene)-propoxy]-phenyl}-2-ethoxy-propionate,
Ethyl 3-{4-[4-(10,11-dihydro-dibenzo[a,d]cyclohepten-5-ylidene)-butoxy]-phenyl}-2-ethoxy-propionate,
3-{4-[3-(10,11-Dihydro-dibenzo[a,d]cyclohepten-5-ylidene)-propoxy]-phenyl}-2-ethoxy-propionic acid,
3-{4-[4-(10,11-Dihydro-dibenzo[a,d]cyclohepten-5-ylidene)-butoxy]-phenyl}-2-ethoxy-propionic acid,
Ethyl 3-{4-[2-(10,11-dihydro-dibenzo[a,d]cyclohepten-5-ylidene)-ethoxy]-phenyl}-2-methoxy-propionate,
Ethyl 3-{4-[3-(10,11-dihydro-dibenzo[a,d]cyclohepten-5-ylidene)-propoxy]-phenyl]-2-methoxy-propionate,
Ethyl 3-{4-[4-(10,11-dihydro-dibenzo[a,d]cyclohepten-5-ylidene)-butoxy]-phenyl}-2-methoxy-propionate,
3-{4-[2-(10,11-Dihydro-dibenzo[a,d]cyclohepten-5-ylidene)-ethoxy]-phenyl}-2-methoxy-propionic acid,
3-{4-[3-(10,11-Dihydro-dibenzo[a,d]cyclohepten-5-ylidene)-propoxy]-phenyl}-2-methoxy-propionic acid,
3-{4-[4-(10,11-Dihydro-dibenzo[a,d]cyclohepten-5-ylidene)-butoxy]-phenyl}-2-methoxy-propionic acid,
Ethyl 3-{4-[2-(10,11-dihydro-dibenzo[a,d]cyclohepten-5-ylidene)-ethoxy]-phenyl}-2-propoxy-propionate,
Ethyl 3-{4-[3-(10,11-dihydro-dibenzo[a,d]cyclohepten-5-ylidene)-propoxy]-phenyl}-2-propoxy-propionate,
Ethyl 3-{4-[4-(10,11-dihydro-dibenzo[a,d]cyclohepten-5-ylidene)-butoxy]-phenyl}-2-propoxy-propionate,
3-{4-[2-(10,11-Dihydro-dibenzo[a,d]cyclohepten-5-ylidene)-ethoxy]-phenyl}-2-propoxy-propionic acid,
3-{4-[3-(10,11-Dihydro-dibenzo[a,d]cyclohepten-5-ylidene)-propoxy]-phenyl}-2-propoxy-propionic acid,
3-{4-[4-(10,11-Dihydro-dibenzo[a,d]cyclohepten-5-ylidene)-butoxy]-phenyl}-2-propoxy-propionic acid, Ethyl 2-ethoxy-3-{4-[2-(11H-5-oxa-10-thia-dibenzo[a,d]
  cyclohepten-11-yl)-ethoxy]-phenyl}-propionate,
Ethyl 2-ethoxy-3-{4-[3-(11H-5-oxa-10-thia-dibenzo[a,d]
  cyclohepten-11-yl)-propoxy]-phenyl}-propionate,
Ethyl 2-ethoxy-3-{4-[4-(11H-5-oxa-10-thia-dibenzo[a,d]
  cyclohepten-11-yl)-butoxy]-phenyl}-propionate,
2-Ethoxy-3-{4-[2-(11H-5-oxa-10-thia-dibenzo[a,d]
  cyclohepten-11-yl)-ethoxy]-phenyl}-propionic acid,
2-Ethoxy-3-{4-[3-(11H-5-oxa-10-thia-dibenzo[a,d]
  cyclohepten-11-yl)-propoxy]-phenyl}-propionic acid,
2-Ethoxy-3-{4-[4-(11H-5-oxa-10-thia-dibenzo[a,d]
  cyclohepten-11-yl)-butoxy]-phenyl}-propionic acid,
Ethyl 3-{4-[2-(11H-5-oxa-10-thia-dibenzo[a,d]cyclohepten-
  11-yl)-ethoxy]-phenyl}-2-methoxy-propionate,
Ethyl 3-{4-[3-(11H-5-oxa-10-thia-dibenzo[a,d]cyclohepten-
  11-yl)-propoxy]-phenyl}-2-methoxy-propionate,
Ethyl 3-{4-[4-(11H-5-oxa-10-thia-dibenzo[a,d]cyclohepten-
  11-yl)-butoxy]-phenyl}-2-methoxy-propionate,
2-Methoxy-3-{4-[2-(11H-5-oxa-10-thia-dibenzo[a,d]
  cyclohepten-11-yl)-ethoxy]-phenyl}-propionic acid,
2-Methoxy-3-{4-[3-(11H-5-oxa-10-thia-dibenzo[a,d]
  cyclohepten-11-yl)-propoxy]-phenyl}-propionic acid,
2-Methoxy-3-{4-[4-(11H-5-oxa-10-thia-dibenzo[a,d]
  cyclohepten-11-yl)-butoxy]-phenyl}-propionic acid,
Ethyl 3-{4-[2-(11H-5-oxa-10-thia-dibenzo[a,d]cyclohepten-
  11-yl)-ethoxy]-phenyl}-2-propoxy-propionate,
Ethyl 3-{4-[3-(11H-5-oxa-10-thia-dibenzo[a,d]cyclohepten-
  11-yl)-propoxy]-phenyl}-2-propoxy-propionate,
Ethyl 3-{4-[4-(11H-5-oxa-10-thia-dibenzo[a,d]cyclohepten-
  11-yl)-butoxy]-phenyl}-2-propoxy-propionate,
3-{4-[2-(11H-5-Oxa-10-thia-dibenzo[a,d]cyclohepten-11-
  yl)-ethoxy]-phenyl}-2-propoxy-propionic acid,
3-{4-[3-(11H-5-Oxa-10-thia-dibenzo[a,d]cyclohepten-11-
  yl)-propoxy]-phenyl}-2-propoxy-propionic acid,
3-{4-[4-(11H-5-Oxa-10-thia-dibenzo[a,d]cyclohepten-11-
  yl)-butoxy]-phenyl}-2-propoxy-propionic acid,
Ethyl 2-methoxy-3-{4-[2-(9H-xanthen-9-yl)ethoxy]
  phenyl}propionate,
2-Methoxy-3-{4-[2-(9H-xanthen-9-yl)ethoxy]
  phenyl}propionic acid,
Ethyl 2-ethoxy-3-{4-[2-(9H-xanthen-9-yl)ethoxy]
  phenyl}propionate,
2-Ethoxy-3-{4-[2-(9H-xanthen-9-yl)ethoxy]
  phenyl}propionic acid,
Ethyl 2-propoxy-3-{4-[2-(9H-xanthen-9-yl)ethoxy]
  phenyl}propionate,
2-Propoxy-3-{4-[2-(9H-xanthen-9-yl)ethoxy]
  phenyl}propionic acid,
Ethyl 2-methoxy-3-{4-[3-(9H-xanthen-9-yl)propoxy]
  phenyl}propionate,
2-Methoxy-3-{4-[3-(9H-xanthen-9-yl)propoxy]
  phenyl}propionic acid,
Ethyl 2-ethoxy-3-{4-[3-(9H-xanthen-9-yl)propoxy]
  phenyl}propionate,
2-Ethoxy-3-{4-[3-(9H-xanthen-9-yl)propoxy]
  phenyl}propionic acid,
Ethyl 2-propoxy-3-{4-[3-(9H-xanthen-9-yl)propoxy]
  phenyl}propionate,
2-Propoxy-3-{4-[3-(9H-xanthen-9-yl)propoxy]
  phenyl}propionic acid,
Ethyl 2-methoxy-3-{4-[4-(9H-xanthen-9-yl)butoxy]
  phenyl}propionate,
2-Methoxy-3-{4-[4-(9H-xanthen-9-yl)butoxy]
  phenyl}propionic acid,
Ethyl 2-ethoxy-3-{4-[4-(9H-xanthen-9-yl)butoxy]
  phenyl}propionate,
2-Ethoxy-3-{4-[4-(9H-xanthen-9-yl)butoxy]
  phenyl}propionic acid,
Ethyl 2-propoxy-3-{4-[4-(9H-xanthen-9-yl)butoxy]
  phenyl}propionate,
2-Propoxy-3-{[4-(9H-xanthen-9-yl)butoxy]
  phenyl}propionic acid,
Ethyl 3-(4-(2-(12H-dibenzo[d,g]-1,3-dioxocine-12-ylidene)
  ethoxy)phenyl)-2-methoxy-propionate,
3-(4-(2-(12H-Dibenzo[d,g]-1,3-dioxocine-12-ylidene)
  ethoxy)phenyl)-2-methoxypropionic acid,
Ethyl 3-(4-(3-(12H-dibenzo[d,g]-1,3-dioxocine-12-ylidene)
  propoxy)phenyl)-2-methoxy-propionate,
3-(4-(3-(12H-Dibenzo[d,g]-1,3-dioxocine-12-ylidene)
  propoxy)phenyl)-2-methoxypropionic acid,
Ethyl 3-(4-(4-(12H-dibenzo[d,g]-1,3-dioxocine-12-ylidene)
  butoxy)phenyl)-2-methoxy-propionate,
3-(4-(4-(12H-Dibenzo[d,g]-1,3-dioxocine-12-ylidene)
  butoxy)phenyl)-2-methoxypropionic acid,
Ethyl 3-(4-(2-(12H-dibenzo[d,g]-1,3-dioxocine-12-ylidene)
  ethoxy)phenyl)-2-ethoxypropionate,
3-(4-(2-(12H-Dibenzo[d,g]-1,3-dioxocine-12-ylidene)
  ethoxy)phenyl)-2-ethoxypropionic acid,
Ethyl 3-(4-(3-(12H-dibenzo[d,g]-1,3-dioxocine-12-ylidene)
  propoxy)phenyl)-2-ethoxy-propionate,
3-(4-(3-(12H-Dibenzo[d,g]-1,3-dioxocine-12-ylidene)
  propoxy)phenyl)-2-ethoxypropionic acid,
Ethyl 3-(4-(4-(12H-dibenzo[d,g]-1,3-dioxocine-12-ylidene)
  butoxy)phenyl)-2-ethoxypropionate,
3-(4-(4-(12H-Dibenzo[d,g]-1,3-dioxocine-12-ylidene)
  butoxy)phenyl)-2-ethoxypropionic acid,
Ethyl 3-(4-(2-(12H-dibenzo[d,g]-1,3-dioxocine-12-ylidene)
  ethoxy)phenyl)-2-propoxy-propionate,
3-(4-(2-(12H-Dibenzo[d,g]-1,3-dioxocine-12-ylidene)
  ethoxy)phenyl)-2-propoxypropionic acid,
Ethyl 3-(4-(3-(12H-dibenzo[d,g]-1,3-dioxocine-12-ylidene)
  propoxy)phenyl)-2-propoxy-propionate,
3-(4-(3-(12H-Dibenzo[d,g]-1,3-dioxocine-12-ylidene)
  propoxy)phenyl)-2-propoxypropionic acid,
Ethyl 3-(4-(4-(12H-dibenzo[d,g]-1,3-dioxocine-12-ylidene)
  butoxy)phenyl)-2-propoxy-propionate,
3-(4-(4-(12H-Dibenzo[d,g]-1,3-dioxocine-12-ylidene)
  butoxy)phenyl)-2-propoxypropionic acid,
Ethyl 2-ethoxy-3-[4-(2-{indeno[2,1-b]pyridin-9-ylidene}-
  ethoxy)-phenyl]-propionate,
2-Ethoxy-3-[4-(2-{indeno[2,1-b]pyridin-9-ylidene)ethoxy)-
  phenyl]-propionic acid,
Ethyl 2-ethoxy-3-{4-[2-(9H-indeno[2,1-b]pyridin-9-yl)-
  ethoxy]-phenyl}-propionate,
2-Ethoxy-3-{4-[2-(9H-indeno[2,1-b]pyridin-9-yl)-ethoxy]-
  phenyl}-propionic acid,
Ethyl 2-ethoxy-3-{4-[2-(1-oxa-cyclopenta[a]inden-8-
  ylidene)-ethoxy]-phenyl}-propionate,
2-Ethoxy-3-{4-[2-(1-oxa-cyclopenta[a]inden-8-ylidene)-
  ethoxy]-phenyl}-propionic acid,
Ethyl 2-ethoxy-3-{4-[2-(8H-1-oxa-cyclopenta[a]inden-8-
  yl)-ethoxy]-phenyl}-propionate,
2-Ethoxy-3-{4-[2-(8H-1-oxa-cyclopenta[a]inden-8-yl)-
  ethoxy]-phenyl}-propionic acid,
Ethyl 2-ethoxy-3-{4-[2-(dibenzo[a,d]cyclohepten-5-
  ylidene)-ethoxy]-phenyl}-propionate,
2-Ethoxy-3-{4-[2-(dibenzo[a,d]cyclohepten-5-ylidene)-
  ethoxy]-phenyl}-propionic acid,
Ethyl 2-ethoxy-3-{4-[2-(10-methyldibenzo[a,d]
  cyclohepten-5-ylidene)-ethoxy]-phenyl}-propionate,
2-Ethoxy-3-{4-[2-(10-methyldibenzo[a,d]cyclohepten-5-
  ylidene)-ethoxy]-phenyl}-propionic acid,
Ethyl 2-ethoxy-3-{4-[2-(10-oxo-10,11-dihydro-dibenzo[a,
  d]cyclohepten-5-ylidene)-ethoxy]-phenyl}-propionate,
2-Ethoxy-3-{4-[2-(10-oxo-10,11-dihydro-dibenzo[a,d]
  cyclohepten-5-ylidene)-ethoxy]-phenyl}-propionic acid, Ethyl 2-ethoxy-3-{4-[2-(10-methyl-10H-acridin-9-ylidene)-ethoxy]-phenyl}-propionate,
2-Ethoxy-3-{4-[2-(10-methyl-10H-acridin-9-ylidene)-ethoxy]-phenyl}-propionic acid,
Ethyl 3-{4-[2-(10H-acridin-9-ylidene)-ethoxy]-phenyl}-2-ethoxy-propionate,
3-{4-[2-(10H-Acridin-9-ylidene)-ethoxy]-phenyl}-2-ethoxy-propionic acid,
Ethyl 2-ethoxy-3-{4-[2-(10-oxo-10H-anthracen-9-ylidene)-ethoxy]-phenyl}-propionate,
2-Ethoxy-3-{4-[2-(10-oxo-10H-anthracen-9-ylidene)-ethoxy]-phenyl}-propionic acid,
Ethyl 2-ethoxy-3-{4-[2-(9H-thioxanthen-9-yl)-ethoxy]-phenyl}-propionate,
Ethyl 2-ethoxy-3-{4-[2-(11H-10-thia-dibenzo[a,d]cyclohepten-5-ylidene)-ethoxy]-phenyl}-propionate;
or a pharmaceutically acceptable salt thereof.

Further preferred compounds of the invention are:
2-Ethoxy-3-[4-(2-xanthen-9-ylidene-ethoxy)-phenyl]-propionic acid,
2-Methoxy-3-[4-(2-xanthen-9-ylidene-ethoxy)-phenyl]-propiohic acid,
2-Ethoxy-3-[4-(2-xanthen-9-ylidene-propoxy)-phenyl]-propionic acid,
2-Ethoxy-3-[4-(2-thioxanthen-9-ylidene-ethoxy)-phenyl]-propionic acid,
2-Methoxy-3-[4-(2-thioxanthen-9-ylidene-ethoxy)-phenyl]-propionic acid,
2-Ethoxy-3-[4-(2-thioxanthen-9-ylidene-propoxy)-phenyl]-propionic acid,
2-Ethoxy-3-{4-[2-(9H-thioxanthen-9-yl)-ethoxy]-phenyl}-propionic acid,
3-{4-[2-(10,11-Dihydro-dibenzo[a,d]cyclohepten-5-ylidene)-ethoxy]-phenyl}-2-ethoxy-propionic acid,
3-{4-[2-(10,11-Dihydro-dibenzo[a,d]cyclohepten-5-ylidene)-propoxy]-phenyl}-2-ethoxy-propionic acid,
3-{4-[2-(6H-Dibenzo[b,e]oxepin-11-ylidene)-ethoxy]-phenyl}-2-ethoxy-propionic acid,
2-Ethoxy-3-{4-[2-(11H-10-thia-dibenzo[a,d]cyclohepten-5-ylidene)-ethoxy]-phenyl}-propionic acid,
3-{4-2-[2-(5,11-Dihydro-10-thia-dibenzo[a,d]cyclohepten-5-yl)-ethoxy]-phenyl}-2-ethoxy-propionic acid,
2-Ethoxy-3-{4-[2-(5-methyl-5,6-dihydro-dibenzo[b,e]azepin-11-ylidene)-ethoxy]-phenyl}-propionic acid,
2-Ethoxy-3-{4-[2-(11-oxo-6,11-dihydro-dibenzo[b,e]azepin-5-yl)-ethoxy]-phenyl}-propionic acid,
3-{4-[2-(6,11-Dihydro-dibenzo[b,e]azepin-5-yl)-ethoxy]-phenyl}-2-ethoxy-propionic acid,
3-{4-[2-(6,11-Dioxo-6,11-dihydro-dibenzo[b,e]azepin-5-yl)-ethoxy]-phenyl}-2-ethoxy-propionic acid,
3-{4-[2-(11H-Dibenzo[b,f][1,4]oxazepin-10-yl)-ethoxy]-phenyl}-2-ethoxy-propionic acid,
3-{4-[2-(11,12-Dihydro-dibenzo[a,e]cycloocten-5-yl)-ethoxy]-phenyl}-2-ethoxy-propionic acid;
or a pharmaceutically acceptable salt thereof.

In the above structural formulas and throughout the present specification, the following terms have the indicated meaning:

The terms "$C_{1-12}$-alkyl" as used herein, alone or in combination is intended to include those alkyl groups of the designated length in either a linear or branched or cyclic configuration. represents e.g. cyclopropyl, cyclobutyl, cyclopentyl, cyclohexyl, cycloheptyl and cyclooctyl and the like. Typical $C_{1-6}$-alkyl groups include, but are not limited to, methyl, ethyl, n-propyl, iso-propyl, butyl, iso-butyl, sec-butyl, tert-butyl, pentyl, iso-pentyl, hexyl, iso-hexyl, cyclopropyl, cyclobutyl, cyclopentyl, cyclohexyl, cycloheptyl and cyclooctyl and the like.

The terms "$C_{2-n'}$-alkenyl" wherein n' can be from 3 through 15, as used herein, represents an olefinically unsaturated branched or straight group having from 2 to the specified number of carbon atoms and at least one double bond. Examples of such groups include, but are not limited to, vinyl, 1-propenyl, 2-propenyl, allyl, iso-proppenyl, 1,3-butadienyl, 1-butenyl, hexenyl, pentenyl, and the like.

The terms "$C_{2-n'}$-alkynyl" wherein n' can be from 3 through 15, as used herein, represent an unsaturated branched or straight group having from 2 to the specified number of carbon atoms and at least one triple bond. Examples of such groups include, but are not limited to, 1-propynyl, 2-propynyl, 1-butynyl, 2-butynyl, 1-pentynyl, 2-pentynyl and the like.

The terms "$C_{4-n'}$-alkenynyl" wherein n' can be from 5 through 15, as used herein, represent an unsaturated branched or straight hydrocarbon group having from 4 to the specified number of carbon atoms and both at least one double bond and at least one triple bond. Examples of such groups include, but are not limited to, 1-penten-4-yne, 3-penten-1-yne, 1,3-hexadiene-5-yne and the like.

The term "$C_{1-12}$-alkoxy" as used herein, alone or in combination is intended to include those $C_{1-12}$alkyl groups of the designated length in either a linear or branched or cyclic configuration linked thorugh an ether oxygen having its free valence bond from the ether oxygen. Examples of linear alkoxy groups are methoxy, ethoxy, propoxy, butoxy, pentoxy and hexoxy. Examples of branched alkoxy are isoprpoxy, sec-butoxy, tert-butoxy, isopentoxy and isohexoxy. Example of cyclic alkoxy are cyclopropyloxy, cyclobutyloxy, cyclopentyloxy and cyclohexyloxy.

The term "$C_{1-6}$-alkoxycarbonyloxy" is intended to include the above defined $C_{1-6}$-alkoxy groups attached to a carbonyloxy moiety, eg. methoxycarbonyloxy, ethoxycarbonyloxy, etc.

As used herein the term "$C_{4-12}$-(cycloalkylalkyl)" represents a branched or straight alkyl group substituted at a carbon with a cycloalkyl group. Examples of such groups include, but are not limited to, cyclopropylethyl, cyclobutylmethyl, 2-(cyclohexyl)ethyl, cyclohexylmethyl, 3-(cyclopentyl)-1-propyl, and the like.

The term "$C_{1-12}$-alkylthio" as used herein, alone or in combination, refers to a straight or branched or cyclic monovalent substituent comprising a $C_{1-12}$-alkyl group linked through a divalent sulfur atom having its free valence bond from the sulfur atom and having 1 to 12 carbon atoms e.g. methylthio, ethylthio, propylthio, butylthio, pentylthio. Example of cyclic alkylthio are cyclopropylthio, cyclobutylthio, cyclopentylthio and cyclohexylthio.

The term "$C_{1-12}$alkylamino" as used herein, alone or in combination, refers to a straight or branched or cyclic monovalent substituent comprising a $C_{1-12}$-alkyl group linked through amino having a free valence bond from the nitrogen atom e.g. methylamino, ethylamino, propylamino, butylamino, pentylamino. Example of cyclic alkylamino are cyclopropylamino, cyclobutylamino, cyclopentylamino and cyclohexylamino.

The term "hydroxy$C_{1-12}$alkyl" as used herein, alone or in combination, refers to a $C_{1-12}$alkyl as defined herein whereto is attached a hydroxy group, e.g. hydroxyethyl, 1-hydroxypropyl, 2-hydroxypropyl etc.

The term "arylamino" as used herein, alone or in combination, refers to an aryl as defined herein linked through amino having a free valence bond from the nitrogen atom e.g. phenylamino, naphthylamino, etc.

The term "aralkylamino" as used herein, alone or in combination, refers to an aralkyl as defined herein linked through amino having a free valence bond from the nitrogen atom e.g. benzylamino, phenethylamino, 3-phenylpropylamino, 1-naphtylmethylamino, 2-(1-naphtyl)ethylamino and the like.

The term "amino$C_{1-12}$alkyl" as used herein, alone or in combination, refers to a $C_{1-12}$alkyl as defined herein whereto is attached an amino group, e.g. aminoethyl, 1-aminopropyl, 2-aminopropyl etc.

The term "aryloxycarbonyl" as used herein, alone or in combination, refers to an aryloxy as defined herein linked through a carbonyl having a free valence bond from the carbon atom, e.g. phenoxycarbonyl, 1-naphthyloxycarbonyl or 2-naphthyloxycarbonyl, etc.

The term "aralkoxycarbonyl" as used herein, alone or in combination, refers to an aralkoxy as defined herein linked through a carbonyl having a free valence bond from the carbon atom, e.g. benzyloxycarbonyl, phenethoxycarbonyl, 3-phenylpropoxycarbonyl, 1-naphthylmethoxycarbonyl, 2-(1-naphtyl)ethoxycarbonyl, etc.

The term "$C_{1-12}$alkoxy$C_{1-12}$alkyl" as used herein, alone or in combination, refers to a $C_{1-12}$alkyl as defined herein whereto is attached a $C_{1-12}$alkoxy as defined herein, e.g. methoxymethyl, ethoxymethyl, methoxyethyl, ethoxyethyl, etc.

The term "aryloxy$C_{1-12}$alkyl" as used herein, alone or in combination, refers to a $C_{1-12}$alkyl as defined herein whereto is attached an aryloxy as defined herein, e.g. phenoxymethyl, phenoxydodecyl, 1-naphthyloxyethyl, 2-naphthyloxypropyl, etc.

The term "aralkoxy$C_{1-12}$alkyl" as used herein, alone or in combination, refers to a $C_{1-12}$alkyl as defined herein whereto is attached an aralkoxy as defined herein, e.g. benzyloxymethyl, phenethoxydodecyl, 3-phenylpropoxyethyl, 1-naphthylmethoxypropyl, 2-(1-naphtyl)ethoxymethyl, etc.

The term "thio$C_{1-12}$alkyl" as used herein, alone or in combination, refers to a $C_{1-12}$alkyl as defined herein whereto is attached a group of formula -SR''' wherein R''' is hydrogen, $C_{1-6}$alkyl or aryl, e.g. thiomethyl, methylthioethyl, phenylthioethyl, etc.

The term "$C_{1-12}$alkoxycarbonylamino" as used herein, alone or in combination, refers to a $C_{1-12}$alkoxycarbonyl as defined herein linked through amino having a free valence bond from the nitrogen atom e.g. methoxycarbonylamino, carbethoxyamino, propoxycarbonylamino, isopropoxycarbonylamino, n-butoxycarbonylamino, tert-butoxycarbonylamino, etc.

The term "aryloxycarbonylamino" as used herein, alone or in combination, refers to an aryloxycarbonyl as defined herein linked through amino having a free valence bond from the nitrogen atom e.g. phenoxycarbonylamino, 1-naphthyloxycarbonylamino or 2-naphthyloxycarbonylamino, etc.

The term "aralkoxycarbonylamino" as used herein, alone or in combination, refers to an aralkoxycarbonyl as defined herein linked through amino having a free valence bond from the nitrogen atom e.g. benzyloxycarbonylamino, phenethoxycarbonylamino, 3-phenylpropoxycarbonylamino, 1-naphthylmethoxycarbonylamino, 2-(1-naphtyl)ethoxycarbonylamino, etc.

The term "aryl" is intended to include aromatic rings, such as carboxylic aromatic rings selected from the group consisting of phenyl, naphthyl, (1-naphtyl or 2-naphtyl) optionally substituted with halogen, amino, hydroxy, $C_{1-6}$-alkyl or $C_{1-6}$-alkoxy.

The term "arylene" is intended to include divalent aromatic rings, such as carboxylic aromatic rings selected from the group consisting of phenylene, naphthylene, optionally substituted with halogen, amino, hydroxy, $C_{1-6}$-alkyl or $C_{1-6}$-alkoxy.

The term "halogen" means fluorine, chlorine, bromine or iodine.

The term "perhalomethyl" means trifluoromethyl, trichloromethyl, tribromomethyl or triiodomethyl.

The term "$C_{1-6}$-dialkylamino" as used herein refers to an amino group wherein the two hydrogen atoms independently are substituted with a straight or branched, saturated hydrocarbon chain having the indicated number of carbon atoms; such as dimethylamino, N-ethyl-N-methylamino, diethylamino, dipropylamino, N-(n-butyl)-N-methylamino, di(n-pentyl)amino, and the like.

The term "acyl" as used herein refers to a monovalent substituent comprising a $C_{1-6}$-alkyl group linked through a carbonyl group; such as e.g. acetyl, propionyl, butyryl, isobutyryl, pivaloyl, valeryl, and the like.

The term "acyloxy" as used herein refers to acyl as defined herein linked to an oxygen atom having its free valence bond from the oxygen atom e.g. acetyloxy, propionyloxy, butyryloxy, isobutyryloxy, pivaloyloxy, valeryloxy, and the like.

The term "$C_{1-12}$-alkoxycarbonyl" as used herein refers to a monovalent substituent comprising a $C_{1-12}$-alkoxy group linked through a carbonyl group; such as e.g. methoxycarbonyl, carbethoxy, propoxycarbonyl, isopropoxycarbonyl, n-butoxycarbonyl, sec-butoxycarbonyl, tert-butoxycarbonyl, 3-methylbutoxycarbonyl, n-hexoxycarbonyl and the like.

The term "a cyclic ring containing from 5 to 7 carbon atoms" as used herein refers to a monocyclic saturated or unsaturated or aromatic system, wherein the ring may be cyclopentyl, cyclopentenyl, cyclohexyl, phenyl or cycloheptyl.

The term "bicycloalkyl" as used herein refers to a monovalent substituent comprising a bicyclic structure made of 6–12 carbon atoms such as e.g. 2-norbornyl, 7-norbornyl, 2-bicyclo[2.2.2]octyl and 9-bicyclo[3.3.1]nonanyl.

The term "heteroaryl" as used herein, alone or in combination, refers to a monovalent substituent comprising a 5–6 membered monocyclic aromatic system or a 9–10 membered bicyclic aromatic system containing one or more heteroatoms selected from nitrogen, oxygen and sulfur, e.g. furan, thiophene, pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine.

The term "heteroarylene" as used herein, alone or in combination, refers to a divalent group comprising a 5–6 membered monocyclic aromatic system or a 9–10 membered bicyclic aromatic system containing one or more heteroatoms selected from nitrogen, oxygen and sulfur, e.g. furan, thiophene, pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine.

The term "heteroaryloxy" as used herein, alone or in combination, refers to a heteroaryl as defined herein linked to an oxygen atom having its free valence bond from the oxygen atom e.g. pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine linked to oxygen.

The term "aralkyl" as used herein refers to a straight or branched saturated carbon chain containing from 1 to 6 carbons substituted with an aromatic carbohydride; such as benzyl, phenethyl, 3-phenylpropyl, 1-naphtylmethyl, 2-(1-naphtyl)ethyl and the like.

The term "aryloxy" as used herein refers to phenoxy, 1-naphthyloxy or 2-naphthyloxy.

The term "aralkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphtyl)ethoxy and the like.

The term "heteroaralkyl" as used herein refers to a straight or branched saturated carbon chain containing from 1 to 6 carbons substituted with a heteroaryl group; such as (2-furyl)methyl, (3-furyl)methyl, (2-thienyl)methyl, (3-thienyl)methyl, (2-pyridyl)methyl, 1-methyl-1-(2-pyrimidyl)ethyl and the like.

The term "heteroaralkoxy" as used herein refers to a heteroaralkyl as defined herein linked to an oxygen atom having its free valence bond from the oxygen atom, e.g. (2-furyl)methyl, (3-furyl)methyl, (2-thienyl)methyl, (3-thienyl)methyl, (2-pyridyl)methyl, 1-methyl-1-(2-pyrimidyl)ethyl linked to oxygen.

The term "$C_{1-6}$-alkylsulfonyl" as used herein refers to a monovalent substituent comprising a $C_{1-6}$-alkyl group linked through a sulfonyl group such as e.g. methylsulfonyl, ethylsulfonyl, n-propylsulfonyl, isopropylsulfonyl, n-butylsulfonyl, sec-butylsulfonyl, isobutylsulfonyl, tert-butylsulfonyl, n-pentylsulfonyl, 2-methylbutylsulfonyl, 3-methylbutylsulfonyl, n-hexylsulfonyl, 4-methylpentylsulfonyl, neopentylsulfonyl, n-hexylsulfonyl and 2,2-dimethylpropylsulfonyl.

The term "$C_{1-6}$-monoalkylaminosulfonyl" as used herein refers to a monovalent substituent comprising a $C_{1-6}$-monoalkylamino group linked through a sulfonyl group such as e.g. methylaminosulfonyl, ethylaminosulfonyl, n-propylaminosulfonyl, isopropylaminosulfonyl, n-butylaminosulfonyl, sec-butylaminosulfonyl, isobutylaminosulfonyl, tert-butylaminosulfonyl, n-pentylaminosulfonyl, 2-methylbutylaminosulfonyl, 3-methylbutylaminosulfonyl, n-hexylaminosulfonyl, 4-methylpentylaminosulfonyl, neopentylaminosulfonyl, n-hexylaminosulfonyl and 2,2-dimethylpropylaminosulfonyl.

The term "$C_{1-6}$-dialkylaminosulfonyl" as used herein refers to a monovalent substituent comprising a $C_{1-6}$-dialkylamino group linked through a sulfonyl group such as dimethylaminosulfonyl, N-ethyl-N-methylaminosulfonyl, diethylaminosulfonyl, dipropylaminosulfonyl, N-(n-butyl)-N-methylaminosulfonyl, di(n-pentyl)aminosulfonyl, and the like.

The term "$C_{1-6}$-alkylsulfinyl" as used herein refers to a monovalent substituent comprising a straight or branched $C_{1-6}$-alkyl group linked through a sulfinyl group (—S(=O)—); such as e.g. methylsulfinyl, ethylsulfinyl, isopropylsulfinyl, butylsulfinyl, pentylsulfinyl, and the like.

The term "acylamino" as used herein refers to an amino group wherein one of the hydrogen atoms is substituted with an acyl group, such as e.g. acetamido, propionamido, isopropylcarbonylamino, and the like.

The term "($C_{3-6}$-cycloalkyl)$C_{1-6}$-alkyl" as used herein, alone or in combination, refers to a straight or branched, saturated hydrocarbon chain having 1 to 6 carbon atoms and being monosubstituted with a $C_{3-6}$-cycloalkyl group, the cycloalkyl group optionally being mono- or polysubstituted with $C_{1-6}$-alkyl, halogen, hydroxy or $C_{1-6}$-alkoxy; such as e.g. cyclopropylmethyl, (1-methylcyclopropyl)methyl, 1-(cyclopropyl)ethyl, cyclopentylmethyl, cyclohexylmethyl, and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy; e.g. phenylthio, (4-methylphenyl)- thio, (2-chlorophenyl)thio, and the like.

The term "arylsulfinyl" as used herein refers to an aryl group linked through a sulfinyl group (—S(=O)—), the aryl group optionally being mono- or polysubstituted with $C_{1-6}$-alkyl, halogen, hydroxy or $C_{1-6}$-alkoxy; such as e.g. phenylsulfinyl, (4-chlorophenyl)sulfinyl, and the like.

The term "arylsulfonyl" as used herein refers to an aryl group linked through a sulfonyl group, the aryl group optionally being mono- or polysubstituted with $C_{1-6}$-alkyl, halogen, hydroxy or $C_{1-6}$-alkoxy; such as e.g. phenylsulfonyl, tosyl, and the like.

The term "$C_{1-6}$-monoalkylaminocarbonyl" as used herein refers to a monovalent substituent comprising a $C_{1-6}$-monoalkylamino group linked through a carbonyl group such as e.g. methylaminocarbonyl, ethylaminocarbonyl, n-propylaminocarbonyl, isopropylaminocarbonyl, n-butylaminocarbonyl, sec-butylaminocarbonyl, isobutylaminocarbonyl, tert-butylaminocarbonyl, n-pentylaminocarbonyl, 2-methylbutylaminocarbonyl, 3-methylbutylaminocarbonyl, n-hexylaminocarbonyl, 4-methylpentylaminocarbonyl, neopentylaminocarbonyl, n-hexylaminocarbonyl and 2-2-dimethylpropylaminocarbonyl.

The term "$C_{1-6}$-dialkylaminocarbonyl" as used herein refers to a monovalent substituent comprising a $C_{1-6}$-dialkylamino group linked through a carbonyl group such as dimethylaminocarbonyl, N-ethyl-N-methylaminocarbonyl, diethylaminocarbonyl, dipropylaminocarbonyl, N-(n-butyl)-N-methylaminocarbonyl, di(n-pentyl)aminocarbonyl, and the like.

The term "$C_{1-6}$-monoalkylaminocarbonylamino" as used herein refers to an amino group wherein one of the hydrogen atoms is substituted with a $C_{1-6}$-monoalkylaminocarbonyl group, e.g. methylaminocarbonylamino, ethylaminocarbonylamino, n-propylaminocarbonylamino, isopropylaminocarbonylamino, n-butylaminocarbonylamino, sec-butylaminocarbonylamino, isobutylaminocarbonylamino, tert-butylaminocarbonylamino, and 2-methylbutylaminocarbonylamino.

The term "$C_{1-6}$-dialkylaminocarbonylamino" as used herein refers to an amino group wherein one of the hydrogen atoms is substituted with a $C_{1-6}$-dialkylaminocarbonyl group, such as dimethylaminocarbonylamino, N-ethyl-N-methylaminocarbonylamino, diethylaminocarbonylamino, dipropylaminocarbonylamino, N-(n-butyl)-N-methylaminocarbonylamino, di(n-pentyl)aminocarbonylamino, and the like.

As used herein, the phrase "heterocyclyl" means a monovalent saturated or unsaturated group being monocyclic and containing one or more, such as from one to four carbon atom(s), and from one to four N, O or S atom(s) or a combination thereof. The phrase "heterocyclyl" includes, but is not limited to, 5-membered heterocycles having one hetero atom (e.g. pyrrolidine, pyrroline); 5-membered heterocycles having two heteroatoms in 1,2 or 1,3 positions (e.g. pyrazoline, pyrazolidine, 1,2-oxathiolane, imidazolidine, imidazoline, 4-oxazolone); 5-membered heterocycles having three heteroatoms (e.g. tetrahydrofurazan);

5-membered heterocycles having four heteroatoms; 6-membered heterocycles with one heteroatom (e.g. piperidine); 6-membered heterocycles with two heteroatoms (e.g. piperazine, morpholine); 6-membered heterocycles with three heteroatoms; and 6-membered heterocycles with four heteroatoms.

As used herein, the phrase "a divalent heterocyclic group" means a divalent saturated or unsaturated system being monocyclic and containing one or more, such as from one to four carbon atom(s), and one to four N, O or S atom(s) or a combination thereof. The phrase a divalent heterocyclic group includes, but is not limited to, 5-membered heterocycles having one hetero atom (e.g. pyrrolidine, pyrroline); 5-membered heterocycles having two heteroatoms in 1,2 or 1,3 positions (e.g. pyrazoline, pyrazolidine, 1,2-oxathiolane, imidazolidine, imidazoline, 4-oxazolone); 5-membered heterocycles having three heteroatoms (e.g. tetrahydrofurazan); 5-membered heterocycles having four heteroatoms; 6-membered heterocycles with one heteroatom (e.g. piperidine); 6-membered heterocycles with two heteroatoms (e.g. piperazine, morpholine); 6-membered heterocycles with three heteroatoms; and 6-membered heterocycles with four heteroatoms.

As used herein, the phrase "a 5–6 membered cyclic ring" means an unsaturated or saturated or aromatic system containing one or more carbon atoms and optionally from one to four N, O or S atom(s) or a combination thereof. The phrase "a 5–6 membered cyclic ring" includes, but is not limited to, e.g. cyclopentyl, cyclohexyl, phenyl, cyclohexenyl, pyrrolidinyl, pyrrolinyl, imidazolidinyl, pyrazolidinyl, pyrazolinyl, piperidyl, piperazinyl, pyrrolyl, 2H-pyrrolyl, imidazolyl, pyrazolyl, triazolyl, pyridyl, pyrazinyl, pyrimidinyl, pyridazinyl, morpholinyl, thiomorpholinyl, isothiazolyl, isoxazolyl, oxazolyl, oxadiazolyl, thiadiazolyl, 1,3-dioxolanyl, 1,4-dioxolanyl, 5-membered heterocycles having one hetero atom (e.g. thiophenes, pyrroles, furans); 5-membered heterocycles having two heteroatoms in 1,2 or 1,3 positions (e.g. oxazoles, pyrazoles, imidazoles, thiazoles, purines); 5-membered heterocycles having three heteroatoms (e.g. triazoles, thiadiazoles); 5-membered heterocycles having four heteroatoms; 6-membered heterocycles with one heteroatom (e.g. pyridine, quinoline, isoquinoline, phenanthridine, cyclohepta[b]pyridine); 6-membered heterocycles with two heteroatoms (e.g. pyridazines, cinnolines, phthalazines, pyrazines, pyrimidines, quinazolines, morpholines); 6-membered heterocycles with three heteroatoms (e.g. 1,3,5-triazine); and 6-membered heterocycles with four heteroatoms.

As used herein, the phrase "5- or 6-membered nitrogen containing ring" refers to a monovalent substituent comprising a monocyclic unsaturated or saturated or aromatic system containing one or more carbon, nitrogen, oxygen or sulfur atoms or a combination thereof and having 5 or 6 members, e.g. pyrrolidinyl, pyrrolinyl, imidazolidinyl, pyrazolidinyl, pyrazolinyl, piperidyl, piperazinyl, pyrrolyl, 2H-pyrrolyl, imidazolyl, pyrazolyl, triazolyl, pyridyl, pyrazinyl, pyrimidinyl, pyridazinyl, morpholinyl, thiomorpholinyl, isothiazolyl, isoxazolyl, oxazolyl, oxadiazolyl, thiadiazolyl, 1,3-dioxolanyl and 1,4-dioxolanyl.

Certain of the above defined terms may occur more than once in the above formula (Ia), and upon such occurence each term shall be defined independently of the other.

Pharmaceutically acceptable salts forming part of this invention include salts of the carboxylic acid moiety such as alkali metal salts like Li, Na, and K salts, alkaline earth metal salts like Ca and Mg salts, salts of organic bases such as lysine, arginine, guanidine, diethanolamine, choline and the like, ammonium or substituted ammonium salts, aluminum salts. Salts may include acid addition salts where appropriate which are, sulphates, nitrates, phosphates, perchlorates, borates, hydrohalides, acetates, tartrates, maleates, citrates, succinates, palmoates, methanesulplionates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

The pharmaceutically acceptable salts are prepared by reacting the compound of formula (Ia) with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guandine and their derivatives etc. may also be used. Alternatively, acid addition salts whereever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et at in "Enantiomers, Racemates and Resolution" (Wiley Interscience, 1981). More specifically the compound of formula (Ia) may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula (Ia) may be prepared by hydrolysing the pure diastereomeric amide.

Various polymorphs of compound of general formula (Ia) forming part of this invention may be prepared by crystallization of compound of formula (Ia) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

The invention also relates to a method of preparing the above mentioned compounds.

A compound of formula (Ia) can be prepared as described below:

By carrying out an alkylation reaction between a compound of formula I, wherein A, n, p, $R^1$, $R^2$, $R^3$, $R^4$, T, X and Z are as defined previously, and LG is a leaving group preferentially chosen from bromide, iodide, methanesulfonate, or 4-toluenesulfonate,

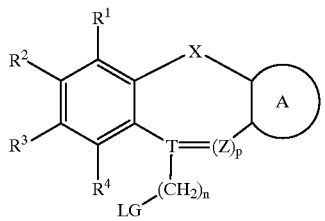

I and a nucleophilic compound of formula II, wherein Ar, m, Q, $R^5$, $R^6$, $R^7$, $R^8$, and Y are as defined previously,

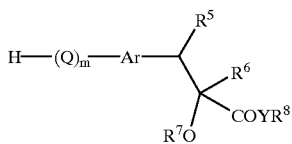

II in the presence of a suitable base such as sodium or potassium carbonate, to give a product of formula III wherein A, Ar, m, n, p, Q, $R^1$, $R^2$, $R^3$, $R^4$, $R^5$, $R^6$, $R^7$, $R^8$, T, X, Y and Z are as defined previously.

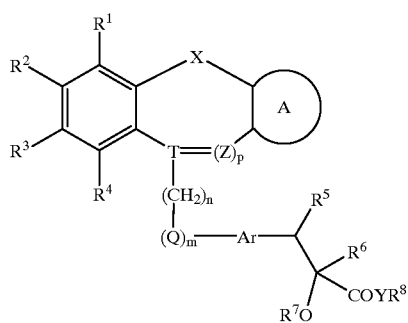

III

Alternatively, by joining a compound of formula I, wherein LG is an alcohol OH group, with a compound of formula II under Mitsunobu conditions, to give a product of formula III, wherein A, Ar, m, n, p, Q, $R^1$, $R^2$, $R^3$, $R^4$, $R^5$, $R^6$, , R $R^8$, T, X, Y and Z are as defined previously.

Alternatively, a compound of formula IV, wherein A, n, p, $R^1$, $R^2$, $R^3$, $R^4$, T, X and Z are as defined previously,

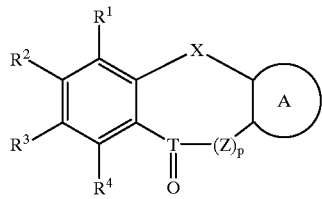

IV may be reacted through a Wittig process with $(Ph_3P)_3P(CH_2)_{n+1}OH.Br$ in the presence of a suitable base such as butyllithium, to give compounds of formula V.

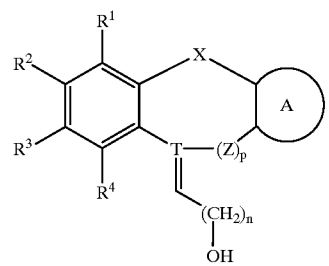

V

Compounds of formula V may then be reacted with compounds of formula II under Mitsunobu conditions to give compounds of formula VI, wherein A, Ar, m, n, p, Q, $R^1$, $R^2$, $R^3$, $R^4$, $R^5$, $R^6$, $R^7$, $R^8$, T, X, Y and Z are as defined previously.

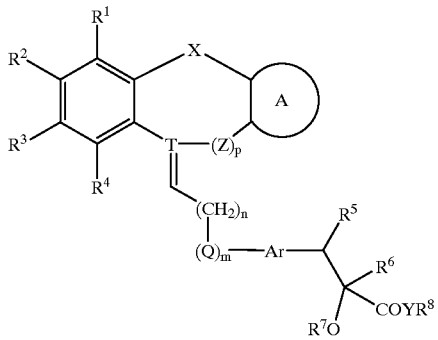

VI

Alternatively, a compound of formula I may be reacted, possibly under transition metal catalysis, with a nucleophilic compound of formula VII,

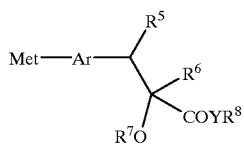

VII wherein "Met" is a metal such as zinc or copper, carrying suitable ligands chosen preferentially from trifluoromethanesulfonate, halide or $C_1$–$C_5$ alkyl, and Ar, $R^5$, $R^6$, $R^7$, $R^8$, and Y are as defined previously, giving rise to products of formula VIII,

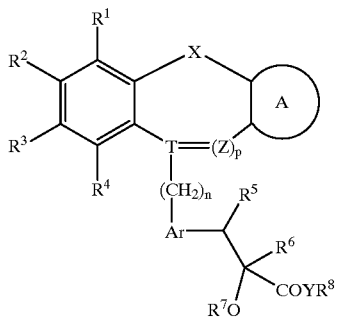

VIII wherein A, Ar, n, p, $R^1$, $R^2$, $R^3$, $R^4$, $R^5$, $R^6$, $R^7$, $R^8$, T, X, Y and Z are as defined previously.

Alternatively, a nucleophilic compound of formula VII, wherein "Met" is as defined previously, may be reacted with an electrophilic compound of formula IX,

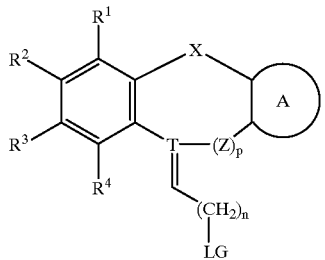

IX giving rise to products of general formula X,

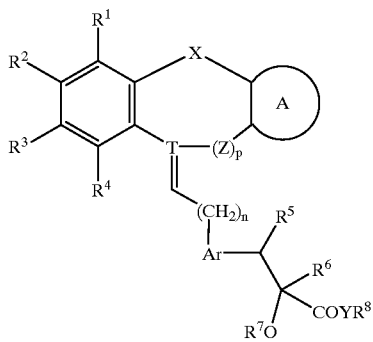

X wherein A, Ar, n, p, $R^1$, $R^2$, $R^3$, $R^4$, $R^5$, $R^6$, $R^7$, $R^8$, T, X, Y and Z are as defined previously.

Compounds of formula III, VI, VIII and X are all belonging to the compounds of formula (Ia).

Pharmacological Methods

In vitro PPAR alpha and PPAR gamma activation activity.

Principle

The PPAR gene transcription activation assays were based on transient transfection into human HEK293 cells of two plasmids encoding a chimeric test protein and a reporter protein respectively. The chimeric test protein was a fusion of the DNA binding domain (DBD) from the yeast GAL4 transcription factor to the ligand binding domain (LBD) of the human PPAR proteins. The PPAR LBD harbored in addition to the ligand binding pocket also the native activation domain (activating function 2=AF2) allowing the fusion protein to function as a PPAR ligand dependent transcription factor. The GAL4 DBD will force the fusion protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand, luciferase protein will be produced in amounts corresponding to the activation of the PPAR protein. The amount of luciferase protein is measured by light emission after addition of the appropriate substrate.

Methods

Cell culture and transfection: HEK293 cells were grown in DMEM+10% FCS, 1% PS. Cells were seeded in 96-well plates the day before transfection to give a confluency of 80% at transfection. 0,8 µg DNA per well was transfected using FuGene transfection reagent according to the manufacturers instructions (Boehringer-Mannheim). Cells were allowed to express protein for 48 h followed by addition of compound.

Plasmids: Human PPAR a and y was obtained by PCR amplification using cDNA templates from liver, intestine and adipose tissue respectively. Amplified cDNAs were cloned into pCR2.1 and sequenced. The LBD from each isoform PPAR was generated by PCR (PPARα: aa 167—C-term; PPARγ: aa 165—C-term) and fused to GAL4-DBD by subcloning fragments in frame into the vector pM1 generating the plasmids pM1αLBD and pM1γLBD. Ensuing fusions were verified by sequencing. The reporter was constructed by inserting an oligonucleotide encoding five repeats of the Gal4 recognition sequence into the pGL2 vector (Promega).

Compounds: All compounds were dissolved in DMSO and diluted 1:1000 upon addition to the cells. Cells were treated with compound (1:1000 in 200 µl growth medium including delipidated serum) for 24 h followed by luciferase assay.

Luciferase assay: Medium including test compound was aspirated and 100 µl PBS incl. 1 mM Mg++ and Ca++ was added to each well. The luciferase assay was performed using the LucLite kit according to the manufacturers instructions (Packard Instruments). Light emission was quantified by counting SPC mode on a Packard Instruments topcounter.

Pharmaceutical Compositions

In another aspect, the present invention includes within its scope pharmaceutical compositions comprising, as an active ingredient, at least one of the compounds of the general formula (Ia) or a pharmaceutically acceptable salt thereof together with a pharmaceutically acceptable carrier or diluent.

Pharmaceutical compositions containing a compound of the present invention may be prepared by conventional techniques, e.g. as described in Remington: The Science and Practise of Pharmacy, $19^{th}$ Ed., 1995. The compositions may appear in conventional forms, for example capsules, tablets, aerosols, solutions, suspensions or topical applications.

Typical compositions include a compound of formula (Ia) or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula (Ia) dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 5 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9–40 T approx. | 0.9 mg |

*Acylated monoglyceride used as plasticizer for film coating.

The compounds of the invention may be administered to a mammal, especially a human in need of such treatment, prevention, elimination, alleviation or amelioration of diseases related to the regulation of blood sugar. Such mammals include also animals, both domestic animals, e.g. household pets, and non-domestic animals such as wildlife.

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen for patients it may frequently be necessary to begin with a dosage of from about 2 to about 70 mg per day and when the condition is under control to reduce the dosage as low as from about 0.1 to about 10 mg per day. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 0.1 to about 100 mg of active ingredient together with a pharmaceutically acceptable carrier per unit dosage.

Usually, dosage forms suitable for oral, nasal, pulmonal or transdermal administration comprise from about 0.001 mg to about 100 mg, preferably from about 0.01 mg to about 50 mg of the compounds of formula (Ia) admixed with a pharmaceutically acceptable carrier or diluent.

In a further aspect, the present invention relates to a method of treating and/or preventing type I or type II diabetes.

In a still further aspect, the present invention relates to the use of one or more compounds of the general formula (Ia) or pharmaceutically acceptable salts thereof for the preparation of a medicament for the treatment and/or prevention of type I or type II diabetes.

Any novel feature or combination of features described herein is considered essential to this invention.

EXAMPLES

The process for preparing compounds of formula Ia, and preparations containing them is further illustrated in the following examples, which however, are not to be construed as limiting.

The structures of the compounds are confirmed by either elemental analysis (MA), proton nuclear magnetic resonance ($^1$H NMR) or mass spectrometry (MS). NMR shifts (δ) are quoted in parts per million (ppm) relative to tetramethylsilane and the signals are quoted showing number of protons in the integration, multiplicity, and coupling constants. Mp indicates melting point and is given in ° C. Column chromatography was carried out using the method described by W. C. Still et al, J. Org. Chem. 1978, 43, 2923–2925 on Macherey Nagel 0.04–0.063 mm silica gel 60 (Art. 815380). Compounds used as starting materials are either known compounds or compounds which can be readily prepared by known methods.

Abbreviations

TLC: Thin Layer Chromatography
DMSO: dimethylsulfoxide
$CDCl_3$: deuterated chloroform
min: minutes
h: hours
ml: millilitres
THF: Tetrahydrofuran
$Et_2O$; diethyl ether
$Na_2SO_4$: anhydrous sodium sulfate
$MgSO_4$: anhydrous magnesium sulfate
s: singlet
d: doublet
t: triplet
q: quartet
$M^+$: Molecular ion Example 1

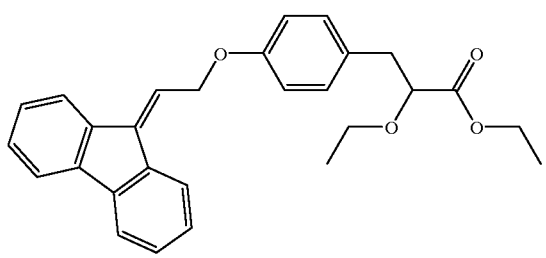

Ethyl 2ethoxy-3-[4-(2-fluoren-9-ylidene-ethoxy)-phenyl]-propionate

Diethyl azodicarboxylate (0.235 ml, 1.49 mmol) was added at 0° C. to a stirred solution of triphenylphosphine (0.392 g, 1.49 mmol) and 2-fluoren-9-ylidene-ethanol (0.208 g, 1.0 mmol) in dry THF (5 ml) and the mixture stirred for 5 min. A solution of ethyl 2-ethoxy-3-(4-hydroxy-phenyl)-propionate (0.356 g, 1.49 mmol) in dry THF (5 ml) was then added, the mixture allowed to warm to room temperature, and stirring continued for 72 h. The resulting mixture was treated with water (50 ml), and the products extracted into dichloromethane (3×20 ml). The extracts were combined, washed with brine, dried ($Na_2SO_4$) and evaporated to a yellow gum. This was then purified by column chromatography on silica gel (15% $Et_2O$ in petroleum eluent) to give ethyl 2-ethoxy-3-[4-(2-fluoren-9-ylidene-ethoxy)-phenyl]-propionate as a yellow gum; 0.28 g (60%).

$^1$H NMR (300 MHz, $CDCl_3$) δ: 1.17 (3H, t, 7 Hz), 1.22 (3H, t, 7 Hz), 2.97 (2H, d, 7 Hz), 3.29–3.40 (1H, m), 3.54–3.66 (1H, m), 3.98 (1H, t, 7 Hz), 4.17 (2H, q, 7 Hz), 5.32 (2H, d, 6 Hz), 6.87 (1H, t, 6 Hz), 6.92 (2H, d, 8 Hz), 7.18 (2H, d, 8 Hz), 7.22–7.45 (4H, m), 7.57–7.77 (4H, m). MS: 428 ($M^+$), 382, 191 (100%).

Example 2

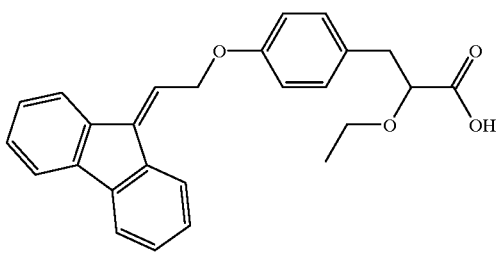

2-Ethoxy-3-[4-(2-fluoren-9-ylidene-ethoxy)-phenyl]-propionic acid

Lithium hydroxide (1M, 1.0 ml, 1.0 mmol) was added to a suspension of ethyl 2-ethoxy-3-[4-(2-fluoren-9-ylidene-ethoxy)-phenyl]-propionate (0.214 g, 0.5 mmol) in ethanol (5 ml) and the resulting mixture heated to gentle reflux for 30 min. The cooled mixture was partitioned between water (30 ml) and dichloromethane (20 ml), acidified to pH 1 by adding 1N hydrochloric acid (3 ml), and the organic phase collected. The aqueous phase was further extracted with dichloromethane (3×20 ml) and the combined organics were washed with brine, dried ($MgSO_4$) and evaporated to give a yellow gum. The product was purified by column chromatography on silica gel (3% methanol in dichloromethane eluent) to give 2-ethoxy-3-[4-(2-fluoren-9-ylidene-ethoxy)-phenyl]-propionic acid, as a yellow solid; 0.104 g (51%).

$^1$H NMR (200 MHz, $CDCl_3$) δ: 1.17 (3H, t, 7 Hz), 2.98 (1H, dd, 14 & 7 Hz), 3.10 (1H, dd, 14 & 4 Hz), 3.40–3.70 (2H, m), 4.06 (1H, dd, 7 & 4 Hz), 5.33 (2H, d, 6 Hz), 6.87 (1H, t, 6 Hz), 6.98 (2H, d, 8 Hz), 7.20 (2H, d, 8 Hz), 7.20–7.47 (4H, m), 7.55–7.80 (4H, m). MS: 400 ($M^+$), 435, 297, 235, 209, 191 (100%), 165.

Example 3

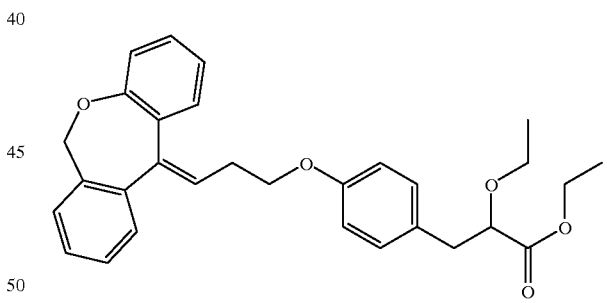

Ethyl 3-{4-[3-(6H-dibenzo[b,e]oxepin-11-ylidene)-propoxy]-phenyl}-2-ethoxy-propionate Diethyl azodicarboxylate (0.235 ml, 1.49 mmol) was added at 0° C. to a stirred solution of triphenylphosphine (0.392 g, 1.49 mmol) and 3-(6H-dibenzo[b,e]oxepin-11-ylidene1-propanol (0.252 g, 1.0 mmol) in dry THF (5 ml) and the mixture stirred for 5 min. A solution of ethyl 2-ethoxy-3-(4-hydroxyphenyl)-propionate (0.356 g, 1.49 mmol) in dry THF (5 ml) was then added, the mixture allowed to warm to room temperature, and stirring continued for 18 h. The resulting mixture was treated with water (50 ml), and the products extracted into dichloromethane (4×50 ml). The extracts were combined, washed with brine, dried ($Na_2SO_4$) and evaporated to an orange gum. This was then purified by column chromatography on silica gel (20% Et₂O in petroleum eluent) to give the title compound as an inseparable 4:1 mixture of E and Z double-bond isomers, as a pale yellow gum; 0.252 g (53%).

¹H NMR (300 MHz, CDCl₃) δ: 1.16 (3H, t, 7 Hz), 1.23 (3H, t, 7 Hz), 2.65 (1.6H, q, 7 Hz, E isomer), 2.90 (0.4H, q, 7 Hz, Z isomer), 2.94 (2H, d, 7 Hz), 3.29–3.40 (1H, m), 3.53–3.67 (1H, m), 3.97 (1H, t, 7 Hz), 4.01 (1.6H, t, 7 Hz, E isomer), 4.08 (0.4H, t, 7 Hz, Z isomer), 4.17 (2H, t, 7 Hz), 4.5–5.7 (2H, very broad m), 5.82 (0.2H, t, 7 Hz, Z isomer), 6.12 (0.8H, t, 7 Hz, E isomer), 6.75–0.90 (4H, m), 7.1–7.4 (8H, m). MS: 472 (M⁺), 426, 341, 326, 235 (100%), 221, 195, 107, 91.

Example 4

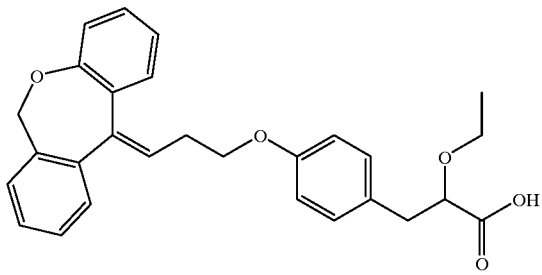

3-{4-[3-(6H-Dibenzo[b,e]oxepin-11-ylidene)-propoxy]-phenyl}-2-ethoxy-propionic acid Sodium hydroxide (1M, 2.5 ml, 2.5 mmol) was added to a solution of a 4:1 E/Z double-bond isomer mixture of ethyl 3-{4-[3-(6H-dibenzo[b,e]oxepin-11-ylidene)-propoxy]-phenyl}2-ethoxy-propionate (0.24 g, 0.51 mmol) in ethanol (5 ml) and the mixture stirred at room temperature for 78 h. The resulting mixture was partitioned between 1N hydrochloric acid (20 ml) and dichloromethane (20 ml), and the organic phase collected. The aqueous phase was further extracted with dichloromethane (3×20 ml) and the combined organics washed with brine, dried (Na₂SO₄) and evaporated to give a pale yellow gum. This was then purified by column chromatography on silica gel (3% methanol in dichloromethane eluent) to give the title compound as an inseparable 4:1 mixture of E and Z double-bond isomers, as a pale yellow glass; 0.186 g (80%).

¹H NMR (200 MHz, CDCl₃) δ: 1.16 (3H, t, 7), 2.65 (1.6H, q, 7, E isomer), 2.90 (0.4H, q, 7 Z isomer), 2.93 (1H, dd, 14 & 9), 3.05 (1H, dd, 14 & 5), 3.32–3.70 (2H, m), 3.94–4.1 (3H, m), 4.5–5.7 (2H, very broad m), 5.80 (0.25H, t, 7, Z isomer), 6.12 (0.75H, t, 7, E isomer), 6.7–6.95 (4H, m), 7.05–7.20 (2H, m), 7.20–7.40 (6H, m). MS: 444 (M⁺), 341, 326, 235 (100%), 221, 195, 107, 91.

Example 5

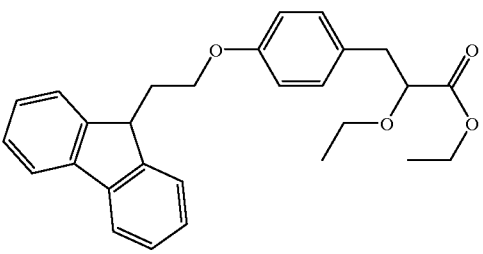

Ethyl 2-ethoxy-3-{4-[2-(9H-fluoren-9-yl)-ethoxy]-phenyl}-propionate

Diethyl azodicarboxylate (0.235 ml, 1.49 mmol) was added at 0° C. to a stirred solution of triphenylphosphine (0.392 g, 1.49 mmol) and 2-(9H-fluoren-9-yl)-ethanol (0.208 g, 1.0 mmol) in dry THF (5 ml) and the mixture stirred for 5 min. A solution of ethyl 2-ethoxy-3-(4-hydroxyphenyl)-propionate (0.356 g, 1.49 mmol) in dry THF (5 ml) was then added, the mixture allowed to warm to room temperature and stirring continued for 20 h. The resulting mixture was treated with water (50 ml), and the products extracted into dichloromethane (4×50 ml). The extracts were combined, washed with brine, dried (Na₂SO₄) and evaporated to a colourless gum. This was then purified by column chromatography on SiO₂ (15% Et₂O in petroleum eluent) to give the title compound as a colourless gum; 0.20 g (47%).

¹H NMR (300 MHz, CDCl₃) δ: 1.17 (3H, t, 7), 1.22 (3H, t, 7), 2.46 (2H, q, 7), 2.93 (2H, d, 7), 3.28–3.40 (1H, m), 3.52–3.65 (1H, m), 3.90 (2H, t, 7), 3.95 (1H, t, 7), 4.16 (2H, q, 7), 4.15–4.28 (1H, m), 6.74 (2H, d, 8), 7.11 (2H, d, 8), 7.25–7.42 (4H, m), 7.52 (2H, q, 8), 7.78 (2H, d, 8), 7.78 (2H, d, 8). MS 430 (M⁺), 384, 299, 193, 179, 165 (100%), 107.

Example 6

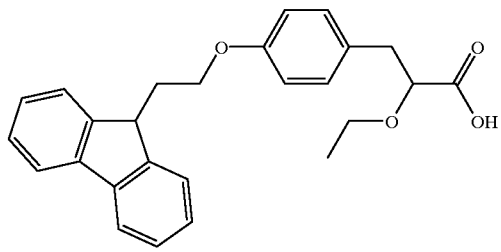

2-Ethoxy-3-{4-[2-(9H-fluoren-9-yl)-ethoxy]-phenyl}-propionic acid

Sodium hydroxide (1M, 2.5 ml, 2.5 mmol) was added to a solution of ethyl 2-ethoxy-3-{4-[2-(9H-fluoren-9-yl)-ethoxy]-phenyl}propionate (0.19 g, 0.44 mmol) in ethanol (5 ml) and the mixture stirred at room temperature for 20 h. The resulting mixture was partitioned between water (20 ml) and dichloromethane (20 ml), acidified to pH 1 by adding 1N hydrochloric acid, and the organic phase collected. The aqueous phase was further extracted with dichloromethane (3×20 ml) and the combined organics were washed with brine, dried (Na₂SO₄) and evaporated to give the title compound as a waxy solid; 0.17 g (95%).

¹NMR (300 MHz, CDCl₃) δ: 1.17 (3H, t, 7), 2.46 (2H, q, 7), 2.93 (1H, dd, 16 & 7), 3.04 (1H, dd, 16 & 5), 3.38–3.50

(1H, m), 3.50–3.65 (1H, m), 3.90 (2H, t, 7), 4.04 (1H, dd, 7 & 5), 4.23 (1H, t, 7), 6.74 (2H, d, 8), 7.11 (2H, d, 8), 7.25–7.42 (4H, m), 7.52 (2H, d, 8), 7.75 (2H, d, 8). MS 402 (M+), 299, 193, 178, 165 (100%), 107.

Example 7

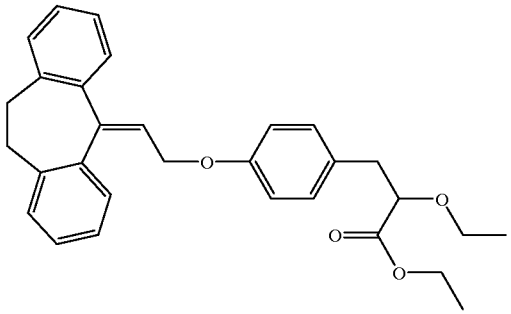

Ethyl 3-{4-[2-(10,11-dihydro-dibenzo[a,d] cyclohepten-5-ylidene)-ethoxy]-phenyl}-2-ethoxy-propionate A mixture of ethyl 2-ethoxy-3-(4-hydroxyphenyl)-propionate (2.38 g, 0.01 mol), 5-(2-bromo-1-ethylidene)-10,11-dihydro-5H-dibenzo[a,d]cycloheptene (2.75 g, 0.01 mol) and potassium carbonate (5.14 g, 0.03 mol) in dimethylformamide (30 ml) was heated at 100° C. for 20 h. The reaction mixture was diluted with benzene (80 ml), washed with 5% aqueous citric acid (3×25 ml) and with saturated NaHCO₃ (25 ml), dried (MgSO₄) and evaporated. The residue (4.88 g) was purified by column chromatography on silica gel (benzene eluent) to yield the title compound; 2.3 g (53.7%).

Rf 0.32 (SiO₂, benzene/chloroform 4:1). ¹H NMR spectrum (250 MHz, CDCl₃) δ: 1.15 (3H, t, 7 Hz), 1.95 (3H, t, 7 Hz), 2.92 (2H, d, J=7 Hz), 3.17 (4H, bs), 3.28 (1H, m), 3.58 (1H, m), 3.94 (1H, dd), 4.14 (2H, q, 7 Hz), 4.59 (2H, bs), 6.10 (1H, t, 7 Hz), 6.71 (2H, dt), 7.05–7.25 (9H, m), 7.32 (1H, m).

Example 8

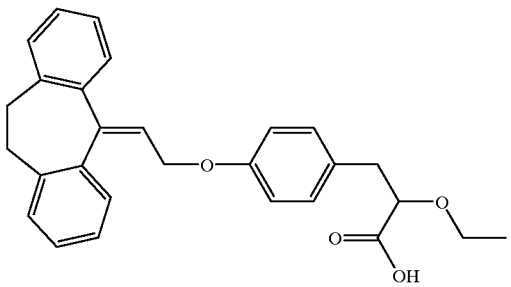

3-{4-[2-(10,11-Dihydro-dibenzo[a,d]cyclohepten-5-ylidene)-ethoxy]-phenyl}-2ethoxy-propionic acid Ethyl 3-4-[2-(10,11-dihydro-dibenzo[a,d]cyclohepten-5-ylidene)-ethoxy]-phenyl}-2-ethoxy-propionate (2.3 g, 53.7 mmol) was dissolved in ethanol (25 ml), 15% sodium hydroxide (7 ml) was added, and the mixture stirred at room temperature for 3 h and stood overnight. The solution was evaporated, water (30 ml) added to the residue, and the mixture acidified to pH 6 with acetic acid (1. 6 ml). The product was extracted with dichloromethane (3×20 ml), and the dichloromethane solution washed with water (20 ml), brine (20 ml), dried (MgSO₄) and evaporated. The residue was crystallised from a mixture of toluene (8 ml) and n-heptane (8 ml) to give the title compound; 1.60 g (74.4%).

M.p. 147–150° C. ¹H NMR spectrum (250 MHz, CDCl₃) δ: 1.15 (3H, t, 7 Hz), 2.99 (2H, m), 3.17 (4H, bs), 3.42–3.58 (2H, m), 4.01 (1H, dd, 8 and 4 Hz), 4.59 (2H, bd), 6.11 (1H, t, 7 Hz), 6.72 (2H, dt), 7.02–7.35 (10H, m). MA: calculated for C₂₈H₂₈O₄ 1/4H₂O: C, 77.66%; H, 6.63%; found: C, 77.81%; H, 6.87%.

Example 9

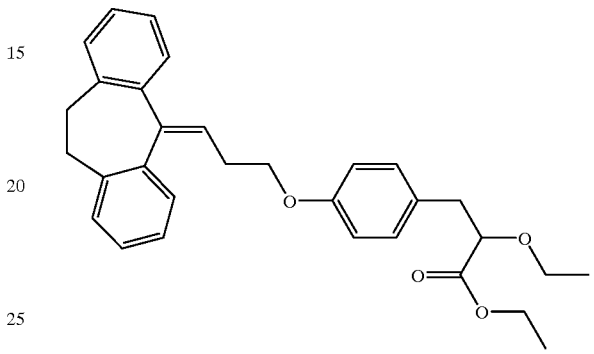

Ethyl 3-(4-(3-(10,11-Dihydro-dibenzo[a,d] cyclohepten-5-ylidene)propoxy)phenyl)-2-ethoxy-propionate A mixture of 5-(3-mesyloxypropylidene)-10,11-dihydro-dibenzo[a,d]cycloheptene (5.0 g, 15.2 mmol), ethyl 3-(4-hydroxyphenyl)-2-ethoxypropionate (3.7 g, 15.5 mmol), potassium carbonate (2.9 g, 21 mmol) and dimethylformamide (10 ml) was heated at 100° C. for 5 h. Benzene (200 ml) and water (200 ml) were added and the phases separated. The organic phase was dried, the solvent evaporated, and the product purified by chromatography on silica gel (benzene/chloroform eluent) to give first 2.5 g of 5-propenylidene-10,11-dihydro-5H-dibenzo(a,d)cycloheptene and then the title compound as an oil; 1.5 g (21%).

¹H NMR (250 MHz, CDCl₃) δ: 0.99 (3H, t), 1.27 (3H, t), 2.69 (2H, q), 3.06 (2H, d), 3.17 (4H, bs), 3.45 (1H, m), 3.68 (1H, m), 4.07 (3H, m), 4.27 (2H, q), 6.06 (1H, t), 6.85 (2H, d), 7.10–7.35 (10H, m).

Example 10

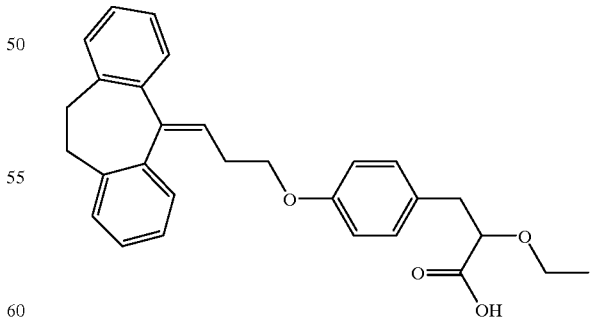

3-(4-(3-(10,11 -Dihydro-dibenzo[a,d]cyclohepten-5-ylidene)propoxy)phenyl)-2-ethoxy-propionic acid L-Lysine salt.

Ethyl 3-(4-(3-(10,11-Dihydro-dibenzo[a,d]cyclohepten-5-ylidene)propoxy)phenyl)-2 -ethoxy-propionate (1.5 g, 3.2 mmol) was dissolved in ethanol (30 ml) and 20% sodium hydroxide (3 ml) added. After 3 days the ethanol was evaporated, water (50 ml) and hydrochloric acid (2 ml) were added, and the mixture extracted with dichloromethane. The organic phase was dried (MgSO$_4$) and the solvent evaporated. The resulting residue (free acid; 1.1 g, 78%) was dissolved in ethanol, treated with L-lysine monohydrate (0.41 g), and the ethanol evaporated. The residue was triturated with diethyl ether, and the crystalline product collected by filtration, and air dried to give the title salt as the dihydrate; 1.45 g.

M.p. 148–150° C. $^1$H NMR (250 MHz, DMSO-d$_6$) δ: 1.03 (3H, t, 7 Hz), 1.66 (6H, bm), 2.51 (2H, bq), 2.70–2.95 (4H, m), 3.07 (4H, bs), 3.31–3.59 (2H, m), 3.76 (1H, m), 4.02 (2H, t, 6 Hz), 5.91 (1H, t, 7 Hz), 6.26 (8H, bs), 6.75 (2H, bd, 8 Hz), 7.00–7.35 (10H, m). MA: calculated for C$_{29}$H$_{30}$O$_4$·C$_6$H$_{14}$N$_2$O$_2$·2H$_2$O: C, 67.28%; H, 7.74%; N, 4.48%; found: C, 67.48%; H, 7.87%; N, 4.68%.

Example 11

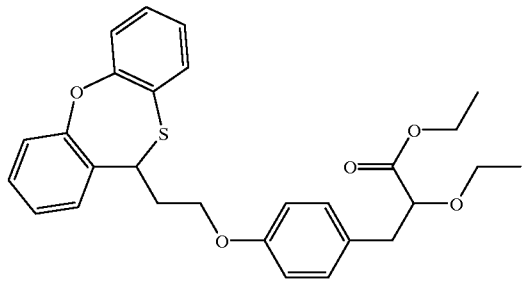

Ethyl 2-ethoxy-3-{4-[2-(11H-5-oxa-10-thia-dibenzo[a,d]cyclohepten-11-yl)-ethoxy]-phenyl}-propionate.

A solution of 2-(11H-5-oxa-10-thia-dibenzo[a,d]cyclohepten-11-yl)-ethanol (4.1 g, 15.9 mmol) and triethylamine (5 ml) in benzene (80 ml) was treated with methanesulfonyl chloride (2.8 g, 24 mmol) and the mixture stirred for 2 h. The resulting reaction mixture was treated with water (50 ml) and the phases were separated. The organic phase was dried (MgSO$_4$) and the solvent evaporated, affording a residue, which was dissolved in dimethylformamide (10 ml). To this solution were added ethyl 3-(4-hydroxyphenyl)-2-ethoxypropionate (3.8 g, 16 mmol) and potassium carbonate (2.8 g, 20 mmol), and the mixture was heated to 100° C. for 10 h. Water (100 ml) and benzene (150 ml) were added, and the organic phase was collected and washed with water (2×50 ml), dried (K$_2$CO$_3$) and evaporated. The resulting residue was purified by column chromatography on silica gel (benzene and chloroform as eluents) to give the title compound as an oil: 4.6 g (60%).

$^1$H NMR (250 MHz, CDCl$_3$) δ1.16 (3H, t), 1.20 (3H, dt, 0.6 and 7 Hz), 2.53–2.80 (2H, m), 2.94 (2H, d, 6.6 Hz), 3.34 (1H, dq, 7.0 and 9.1 Hz), 3.59 (1H, dq, 7 and 9.1 Hz), 3.96 (1H, m), 4.00 (1H, m), 4.15 (2H, q), 4.18 (1H, m), 4.70 (1H, dd, 6.9 and 8.5 Hz), 6.80 (2H, t), 6.93 (1H, ddd, 1.5, 6.8 and 7.8 Hz), 7.01–7.26 (9H, m).

Example 12

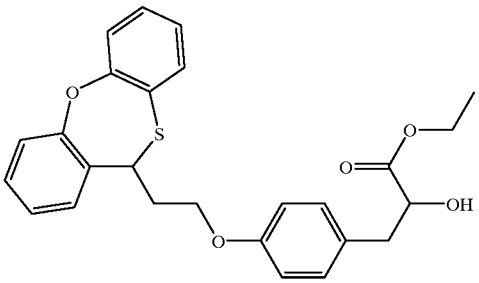

2-Ethoxy-3-{4-[2-(11H-5-oxa-10-thia-dibenzo[a,d]cyclohepten-11-yl)-ethoxy]-phenyl}-propionic acid L-lysine salt Ethyl 2-ethoxy-3-{4-[2-(11H-5-oxa-10-thia-dibenzo[a,d]cyclohepten-11-yl)-ethoxy]-phenyl}-propionate (4.6 g, 9.6 mmol) was dissolved in ethanol (90 ml) and 20% sodium hydroxide (9 ml) was added. After 3 days the ethanol was evaporated, water (50 ml) and hydrochloric acid (6 ml) were added, and the mixture was extracted with dichloromethane. The organic phase was dried (MgSO$_4$) and the solvent evaporated. The resulting residue (3.8 g, 88%) was dissolved in ethanol, treated with L-lysine (1.25 g), the solvent evaporated and the residue triturated with diethyl ether. The resulting crystalline product was collected by filtration and air dried to give the title salt: 4.35 g.

M.p. 153.5–154.5° C. $^1$H NMR (250 MHz, DMSO-d$_6$) δ: 1.00 (3H, bt), 1.2–2.0 (6H, bm), 2.4–3.0 (6H, bm), 3.15 (1H, bm); 3.43 (1H, bm), 3.56 (1H, bm), 3.66 (1H, bs), 4.00 (1H, bs), 4.13 (1H, bs), 4.90 (1H, t, 6.7 Hz), 6.82 (2H, d, 7.9 Hz), 7.00–7.50 (10H, m), 7.82 (5H, bs). MA: calculated for C$_{26}$H$_{26}$O$_5$S·C$_6$H$_{14}$O$_2$N$_2$·1/4H$_2$O: C, 63.93%; H, 6.79%; N, 4.66%; S, 5.33%; found: C, 63.90%; H, 7.09%; N, 4.63%; S, 5.41%.

Example 13

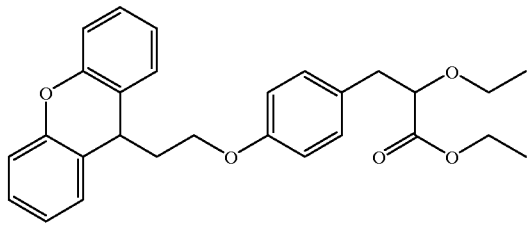

Ethyl 2-ethoxy-3-{4-[2-(9H-xanthen-9-yl)ethoxy]phenyl}propionate

Diethyl azodicarboxylate (40% solution in toluene, 1.61 g, 9.3 mmol) was added dropwise, under argon, over 10 min to a solution of ethyl 3-(4-hydroxyphenyl)-2-ethoxypropionate (2.23 g, 9.3 mmol) and triphenylphosphine (2.43 g, 9.3 mmol) in THF (45 ml). The mixture was stirred for 15 min, then a solution of 2-(9H-xanthen-9-yl)ethanol (2.0 g, 9.3 mmol) in THF (10 ml) was added dropwise over 10 min. The resulting mixture was stirred at room temperature for 60 h. The solvent was evaporated, the residue stirred with benzene (20 ml) and the resulting crystalline solid filtered off. The filtrate was evaporated and the residue purified by column chromatography on silica gel (benzene eluent) to give the title compound as an oil: (1.9 g, 45.8%).

Rf 0.55 (SiO$_2$, benzene/chloroform 4:1). $^1$H NMR (250 MHz, CDCl$_3$) δ: 1.16 (3H, t), 1.21 (3H, t), 2.09 (2H, q) 2.94 (2H, bt), 3.35 (1H, m), 3.60 (1H, m), 3.81 (2H, t), 3.97 (1H, t), 4.15 (2H, q), 4.27 (1H, t), 6.75 (2H, bd), 6.98–7.25 (10H, m), 7.34 (2H, s).

Example 14

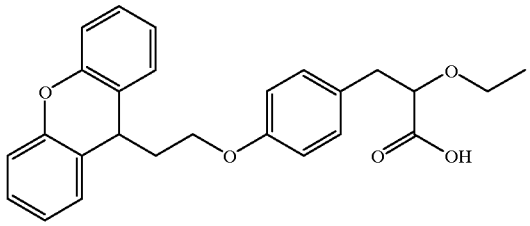

2-Ethoxy-3-{4-[2-(9H-xanthen-9-yl)ethoxy] phenyl}propionic acid

To a solution of ethyl 2-ethoxy-3-{4-[2-(9H-xanthen-9-yl)ethoxy]phenyl}propionate (1.8 g, 4.03 mmol) in ethanol (15 ml) was added a 15% solution of NaOH (4 ml), and the mixture was stirred at room temperature for 5 h, then left to stand overnight. The resulting solution was evaporated, water (50 ml) was added, the mixture was acidified with 15% hydrochloric acid to pH 2, and the products extracted into Et$_2$O (4×30 ml). The combined extracts were washed with water (30 ml), brine (15 ml), dried (MgSO$_4$) and evaporated to give the title compound as an oil: 1.3 g (77.1%).

$^1$H NMR spectrum (250 MHz, CDCl$_3$) δ: 1.17 (3H, t, 6.4 Hz), 2.11 (2H, q, 6.4 Hz), 2.80–3.20 (2H, m), 3.40–3.70 (3H, m), 3.82 (2H, t, 6.8 Hz), 4.04 (1H, dd, 4.3 and 7.6 Hz), 4.28 (1H, t, 6.8 Hz), 6.77 (2H, d, 8.6 Hz), 7.01–7.24 (10H, m).

Example 15

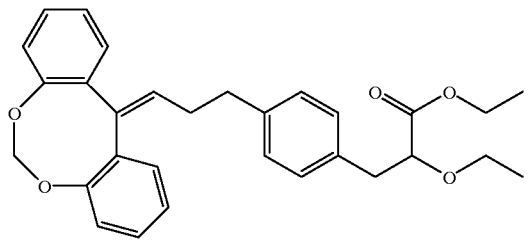

Ethyl 3-(4-(12H-dibenzo[d,g]-1,3-dioxocine-12-ylidene)ethoxy)phenyl)-2-ethoxypropionate A mixture of ethyl 3-(4-hydroxyphenyl)-2-ethoxypropionate (0.96 g, 4.0 mmol), 12-(2-bromoethylidene)-12H-dibenzo[d,g]-1,3-dioxocine (1.07 g, 3.3 mmol) and potassium carbonate (0.45 g, 4.5 mmol) in dimethylformamide (15 ml) was heated to 60° C. for 8.5 h. The reaction mixture was diluted with benzene (50 ml), washed with water (2×20 ml), dried (MgSO$_4$) and evaporated. The residue (1.95 g) was purified by column chromatography on silica gel (benzene and benzene/ethyl acetate (9:1) eluents). The benzene fractions were discarded, whilst the benzene/ethyl acetate fractions were evaporated to give the title compound as an oil: 0.97 g (62%).

Rf 0.35 (SiO$_2$, cyclohexane/ethyl acetate 5:1). $^1$H NMR spectrum (250 MHz, CDCl$_3$) δ: 1.15 (3H, t, 7 Hz), 1.20 (3H, t, 7.2 Hz), 2.93 (2H, d, 7.1 Hz), 3.33 (1H, m), 3.58 (1H, m), 3.95 (1H, t, 7.2 Hz), 4.14 (2H, q, 7.2 Hz), 4.47 (2H, d, 6.2 Hz), 5.90 (2H, s), 6.21 (1H, t, 6.2 Hz), 6.73 (2H, d, 8.2 Hz), 6.93–7.32 (7H, m), 7.35 (2H, m), 7.38 (1H, m).

Example 16

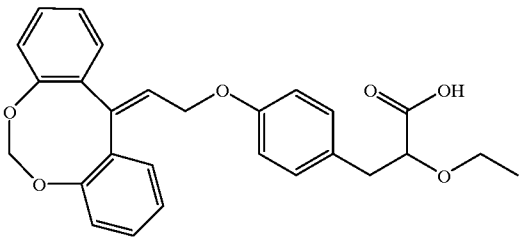

3-(4-(2-(12H-Dibenzo[d,g]-1,3-dioxocine-12-ylidene)ethoxy)phenyl)-2ethoxypropionic acid L-Lysine salt A 15% aqueous solution of NaOH (4 ml) was added to a solution of ethyl 3-(4-(2-(12H-dibenzo(d,g)-1,3-dioxocine-12-ylidene)ethoxy)phenyl)-2-ethoxypropionate (0.95 g, 2.0 mmol) in ethanol (15 ml), and the mixture stirred at room temperature for 2 h, then left to stand overnight. The resulting solution was evaporated, water (20 ml) and benzene (25 ml) were added, and the mixture acidified to pH 6 with acetic acid. The benzene layer was separated, and the water layer further extracted with benzene (2×10 ml). The combined benzene extracts were washed with water (20 ml), brine (15 ml), dried (MgSO$_4$) and evaporated to give 3-(4-(2-(12H-dibenzo(d,g)-1,3-dioxocine-12-ylidene)ethoxy) phenyl)-2-ethoxypropionic acid: 0.79 g (83.2%)

This acid (0.76 g, 1.6 mmol) was dissolved in acetone (30 ml), L-lysine (0.234 g, 1.6 mmol) and water (3 ml) were added and the mixture stirred at room temperature for 2 h. The solution was filtered, evaporated, and the residue stirred with a mixture of Et$_2$O (20 ml) and acetone (20 ml) overnight. The resulting solid was collected by filtration, washed with Et$_2$O (2×30 ml) and dried to give the title compound as a partial hydrate: 0.90 g (93.5%).

M.p. 162–168° C. $^1$H NMR (250 MHz, DMSO-d$_6$) δ: 1.04 (3H, t, 6.8 Hz), 1.38–1.89 (6H, m), 2.75 (3H, m), 2.90 (1H, dd, 14.4 and 4.3 Hz), 3.27 (3H, m), 3.58 (1H, m), 3.75 (1H, m) 4.49 (2H, d, 6.9 Hz), 5.89 (10H, bs), 6.20 (1H, t, 6.3 Hz), 6.75 (2H, d, 7.7 Hz), 6.91–7.52 (10H, m). MA: calculated for C$_{27}$H$_{26}$O$_6$·C$_6$H$_{14}$N$_2$O$_2$·1/2H$_2$O: C, 65.87%; H, 6.87%; N, 4.66%; found: C, 65.43%; H, 6.98%; N, 4.92%.

What is claimed is:

1. A compound of formula (Ia)

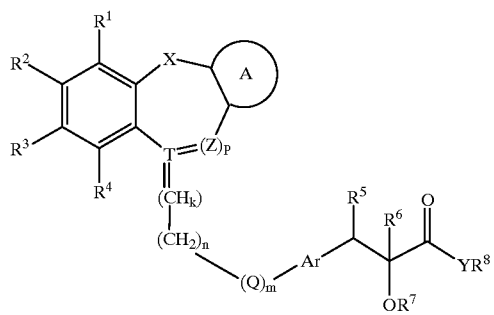

(Ia)

wherein R$^1$, R$^2$, R$^3$, and R$^4$ independently of each other represent hydrogen, halogen, perhalomethyl, hydroxy, nitro, cyano, formyl, or $C_{1-12}$alkyl, $C_{4-12}$-alkenynyl, $C_{2-12}$-alkenyl, $C_{2-12}$-alkynyl, $C_{1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-12}$ alkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR$^{11}$, or —SO$_2$R$^{12}$, wherein R$^{11}$ and R$^{12}$ independently of each other are selected from hydroxy, halogen, perhalomethyl, $C_{1-6}$alkoxy or amino optionally substituted with one or more $C_{1-6}$alkyl, perhalomethyl or aryl; optionally substituted with one or more halogen, perhalomethyl, hydroxy, nitro or cyano; or R$^1$ and R$^2$, R$^2$ and R$^3$ and/or R$^3$ and R$^4$ may form a cyclic ring containing from 5 to 7 carbon atoms optionally substituted with one or more $C_{1-6}$alkyl; ring A is benzo, optionally substituted with one or more halogen, perhalomethyl, hydroxy, nitro, cyano, formyl, or $C_{1-12}$alkyl, $C_{4-12}$-alkenynyl, $C_{2-12}$-alkenyl, $C_{2-12}$-alkynyl, $C_{1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-12}$alkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR$^{11}$, or —SO$_2$R$^{12}$, wherein R$^{11}$ and R$^{12}$ independently of each other are selected from hydroxy, halogen, perhalomethyl, $C_{1-6}$alkoxy or amino optionally substituted with one or more $C_{1-6}$alkyl, perhalomethyl or aryl; optionally substituted with one or more halogen, perhalomethyl, hydroxy, nitro or cyano;

X is —O— or —S—;

T is >CH—;

Q is —O—, —S—, >SO$_2$, >NR$^{12}$, wherein R$^{12}$ is hydrogen, halogen, hydroxy, nitro, cyano, formyl, $C_{1-12}$alkyl, $C_{1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR$^{17}$, or —SO$_2$R$^{18}$, wherein R$^{17}$ and R$^{18}$ independently of each other are selected from hydroxy, halogen, $C_{1-6}$alkoxy, amino optionally substituted with one or more $C_{1-6}$alkyl, perhalomethyl or aryl;

k is 1 or 2;

T==(CH)$_k$ independently of each other represents a single bond or a double bond, provided that both are not a double bond at the same time;

Ar is phenylene optionally substituted with one or more $C_{1-6}$alkyl or aryl;

R$^5$ represents hydrogen, hydroxy, halogen, $C_{1-12}$alkoxy, $C_{1-12}$alkyl, $C_{4-12}$-alkenynyl, $C_{2-12}$-alkenyl, $C_{2-12}$-alkynyl or aralkyl; optionally substituted with one or more halogen, perhalomethyl, hydroxy, nitro or cyano; or R$^5$ forms a bond together with R$^6$;

R$^6$ represents hydrogen, hydroxy, halogen, $C_{1-12}$alkoxy, $C_{1-12}$alkyl, $C_{4-12}$-alkenynyl, $C_{2-12}$-alkenyl, $C_{2-12}$-alkynyl, acyl or aralkyl; optionally substituted with one or more halogen, perhalomethyl, hydroxy, nitro or cyano; or R$^6$ forms a bond together with R$^5$;

R$^7$ represents hydrogen, $C_{1-12}$alkyl, $C_{4-12}$-alkenynyl, $C_{2-12}$-alkenyl, $C_{2-12}$-alkynyl, aryl, aralkyl, $C_{1-12}$alkoxy$C_{1-12}$alkyl, $C_{1-12}$alkoxycarbonyl, aryloxycarbonyl, $C_{1-12}$alkylaminocarbonyl, arylaminocarbonyl, acyl, heterocyclyl, heteroaryl or heteroaralkyl groups; optionally substituted with one or more halogen, perhalomethyl, hydroxy, nitro or cyano;

R$^8$ represents hydrogen, $C_{1-12}$alkyl, $C_{4-12}$-alkenynyl, $C_{2-12}$-alkenyl, $C_{2-12}$-alkynyl, aryl, aralkyl, heterocyclyl, heteroaryl or heteroaralkyl groups; optionally substituted with one or more halogen, perhalomethyl, hydroxy, nitro or cyano;

Y represents oxygen, sulphur or NR$^{10}$, where R$^{10}$ represents hydrogen, $C_{1-12}$alkyl, aryl, hydroxy$C_{1-12}$alkyl or aralkyl groups or when Y is NR$^{10}$, R$^8$ and R$^{10}$ may form a 5 or 6 membered nitrogen containing ring, optionally substituted with one or more $C_{1-6}$alkyl;

n is an integer ranging from 0 to 3;

m is an integer ranging from 0 to 1;

p is 0;

or a pharmaceutically acceptable salt thereof.

2. A compound according to claim 1 wherein R$^1$, R$^2$, R$^3$, and R$^4$ independently of each other represent hydrogen, halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-7}$alkyl, amino, acylamino, $C_{1-7}$alkyl-amino, arylamino, aralkylamino, amino$C_{1-7}$alkyl, $C_{1-7}$alkoxy$C_{1-7}$ alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino, aralkoxycarbonylamino, —COR$^{11}$, or —SO$_2$R$^{12}$, wherein R$^{11}$ and R$^{12}$ independently of each other are selected from hydroxy, perhalomethyl, $C_{1-6}$alkoxy or amino optionally substituted with one or more $C_{1-6}$alkyl, perhalomethyl or aryl; optionally substituted with one or more halogen, perhalomethyl, hydroxy, or cyano; or R$^1$ and R$^2$, R$^2$ and R$^3$ and/or R$^3$ and R$^4$ may form a cyclic ring containing from 5 to 7 carbon atoms optionally substituted with one or more $C_{1-6}$alkyl.

3. A compound according to claim 1 wherein ring A is benzo, optionally substituted with one or more halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-7}$alkyl, amino, acylamino, $C_{1-7}$alkyl-amino, arylamino, aralkylamino, amino$C_{1-7}$alkyl, $C_{1-7}$alkoxy$C_{1-7}$ alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino, aralkoxycarbonylamino, —COR$^{11}$, or —SO$_2$R$^{12}$, wherein R$^{11}$ and R$^{12}$ independently of each other are selected from hydroxy, perhalomethyl, or amino optionally substituted with one or more $C_{1-6}$alkyl, perhalomethyl or aryl; optionally substituted with one or more halogen, perhalomethyl, hydroxy, or cyano.

4. A compound according to claim 1 wherein Q is —O—, —S— or >NR$^{12}$, wherein R$^{12}$ is hydrogen, or methyl.

5. A compound according to claim 1 wherein R$^5$ represents hydrogen, hydroxy, halogen, $C_{1-7}$alkoxy, $C_{1-7}$alkyl, $C_{4-7}$-alkenynyl, $C_{2-7}$-alkenyl, $C_{2-7}$-alkynyl or aralkyl, or R$^5$ forms a bond together with R$^6$.

6. A compound according to claim 1 wherein R$^6$ represents hydrogen, $C_{1-7}$alkoxy, $C_{1-7}$alkyl, $C_{4-7}$-alkenynyl, $C_{2-7}$- alkenyl, $C_{2-7}$-alkynyl, acyl or aralkyl, or $R^6$ forms a bond together with $R^5$.

7. A compound according to claim 1 wherein $R^7$ represents hydrogen, $C_{1-7}$alkyl, $C_{4-7}$-alkenynyl, $C_{2-7}$-alkenyl, $C_{2-7}$-alkynyl, aryl, aralkyl, $C_{1-7}$alkoxy$C_{1-7}$alkyl, $C_{1-7}$alkoxycarbonyl, aryloxycarbonyl, $C_{1-7}$alkylaminocarbonyl, arylaminocarbonyl, acyl, heterocyclyl, heteroaryl or heteroaralkyl groups.

8. A compound according to claim 1 wherein $R^8$ represents hydrogen, $C_{1-7}$alkyl, $C_{4-7}$-alkenynyl, $C_{2-7}$-alkenyl, $C_{2-7}$-alkynyl, aryl, aralkyl, heterocyclyl, heteroaryl or heteroaralkyl groups; optionally substituted with one or more halogen, perhalomethyl, hydroxy, nitro or cyano.

9. A compound according to claim 1 wherein Y represents oxygen, sulphur or $NR^{10}$, where $R^{10}$ represents hydrogen, $C_{1-7}$alkyl, aryl, hydroxy$C_{1-7}$alkyl or aralkyl groups.

10. The compound according to claim 1 which is:
2-Ethoxy-3-[4-(2-xanthen-9-ylidene-ethoxy)-phenyl]-propionic acid,
2-Methoxy-3-[4-(2-xanthen-9-ylidene-ethoxy)-phenyl]-propionic acid,
2-Ethoxy-3-[4-(2-xanthen-9-ylidene-propoxy)-phenyl]-propionic acid,
2-Ethoxy-3-[4-(2-thioxanthen-9-ylidene-ethoxy)-phenyl]-propionic acid,
2-Methoxy-3-[4-(2-thioxanthen-9-ylidene-ethoxy)-phenyl]-propionic acid,
2-Ethoxy-3-[4-(2-thioxanthen-9-ylidene-propoxy)-phenyl]-propionic acid,
Ethyl 2-methoxy-3-{4-[2-(9H-xanthen-9-yl)ethoxy]phenyl}propionate,
2-Methoxy-3-{4-[2-(9H-xanthen-9-yl)ethoxy]phenyl}propionic acid,
Ethyl 2-ethoxy-3-{4-[2-(9H-xanthen-9-yl)ethoxy]phenyl}propionate,
2-Ethoxy-3-{4-[2-(9H-xanthen-9-yl)ethoxy]phenyl}propionic acid,
Ethyl 2-propoxy-3-{4-[2-(9H-xanthen-9-yl)ethoxy]phenyl}propionate,
2-Propoxy-3-{4-[2-(9H-xanthen-9-yl)ethoxy]phenyl}propionic acid,
Ethyl 2-methoxy-3-{4-[3-(9H-xanthen-9-yl)propoxy]phenyl}propionate,
2-Methoxy-3-{4-[3-(9H-xanthen-9-yl)propoxy]phenyl}propionic acid,
Ethyl 2-ethoxy-3-{4-[3-(9H-xanthen-9-yl)propoxy]phenyl}propionate,
2-Ethoxy-3-{4-[3-(9H-xanthen-9-yl)propoxy]phenyl}propionic acid,
Ethyl 2-propoxy-3-{4-[3-(9H-xanthen-9-yl)propoxy]phenyl}propionate,
2-Propoxy-3-{4-[3-(9H-xanthen-9-yl)propoxy]phenyl}propionic acid,
Ethyl 2-methoxy-3-{4-[4-(9H-xanthen-9-yl)butoxy]phenyl}propionate,
2-Methoxy-3-{4-[4-(9H-xanthen-9-yl)butoxy]phenyl}propionic acid,
Ethyl 2-ethoxy-3-{4-[4-(9H-xanthen-9-yl)butoxy]phenyl}propionate,
2-Ethoxy-3-{4-[4-(9H-xanthen-9-yl)butoxy]phenyl}propionic acid,
Ethyl 2-propoxy-3-{4-[4-(9H-xanthen-9-yl)butoxy]phenyl}propionate,
2-Propoxy-3-{4-[4-(9H-xanthen-9-yl)butoxy]phenyl}propionic acid,
Ethyl 2-ethoxy-3-{4-[2-9H-thioxanthen-9-yl)-ethoxy]-phenyl}-propionate,
or a pharmaceutically acceptable salt thereof.

11. The compound according to claim 1 which is:
2-Ethoxy-3-[4-(2-xanthen-9-ylidene-ethoxy)-phenyl]-propionic acid,
2-Methoxy-3-[4-(2-xanthen-9-ylidene-ethoxy)-phenyl]-propionic acid,
2-Ethoxy-3-[4-(2-xanthen-9-ylidene-propoxy)-phenyl]-propionic acid,
2-Ethoxy-3-[4-(2-thioxanthen-9-ylidene-ethoxy)-phenyl]-propionic acid,
2-Methoxy-3-[4-(2-thioxanthen-9-ylidene-ethoxy)-phenyl]-propionic acid,
2-Ethoxy-3-[4-(2-thioxanthen-9-ylidene-propoxy)-phenyl]-propionic acid,
2-Ethoxy-3-{4-[2-(9H-thioxanthen-9-yl)-ethoxy]-phenyl}-propionic acid,
or a pharmaceutically acceptable salt thereof.

12. A pharmaceutical composition comprising, as an active ingredient, a compound according to claim 1 or a pharmaceutically acceptable salt thereof together with a pharmaceutically acceptable carrier or diluent.

13. A method for the treatment of diabetes, the method comprising administering to a subject in need thereof an effective amount of a compound according to claim 1 or a pharmaceutically acceptable salt thereof.

14. A method for treatment of obesity, the method comprising administering to a subject in need thereof an effective amount of a compound according to claim 1 or a pharmaceutically acceptable salt thereof.

* * * * *